US008455438B2

(12) United States Patent
Burnett, Jr. et al.

(10) Patent No.: US 8,455,438 B2
(45) Date of Patent: Jun. 4, 2013

(54) NATRIURETIC POLYPEPTIDES FOR REDUCING OR PREVENTING RESTENOSIS

(75) Inventors: John C. Burnett, Jr., Rochester, MN (US); Horng H. Chen, Rochester, MN (US); Ondrej Lisy, Chattanooga, TN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/142,537

(22) PCT Filed: Dec. 29, 2009

(86) PCT No.: PCT/US2009/069687
§ 371 (c)(1),
(2), (4) Date: Jun. 28, 2011

(87) PCT Pub. No.: WO2010/078325
PCT Pub. Date: Jul. 8, 2010

(65) Prior Publication Data
US 2011/0269684 A1 Nov. 3, 2011

Related U.S. Application Data

(60) Provisional application No. 61/141,127, filed on Dec. 29, 2008.

(51) Int. Cl.
C07K 14/58 (2006.01)
C12P 21/04 (2006.01)

(52) U.S. Cl.
USPC ......................................... 514/12.4; 435/69.7

(58) Field of Classification Search
None
See application file for complete search history.

(56) References Cited

U.S. PATENT DOCUMENTS

| | | | |
|---|---|---|---|
| 4,034,074 A | 7/1977 | Miles | |
| 4,098,876 A | 7/1978 | Piasio et al. | |
| 4,161,521 A | 7/1979 | Veber et al. | |
| 4,233,402 A | 11/1980 | Maggio et al. | |
| 4,749,688 A * | 6/1988 | Haslanger et al. | 514/15.7 |
| 4,757,048 A | 7/1988 | Lewicki et al. | |
| 4,935,492 A | 6/1990 | Lewicki et al. | |
| 5,296,347 A | 3/1994 | LaMotte, III | |
| 5,580,859 A | 12/1996 | Felgner et al. | |
| 5,589,466 A | 12/1996 | Felgner et al. | |
| 6,818,619 B2 | 11/2004 | Burnett, Jr. et al. | |
| 7,384,917 B2 | 6/2008 | Burnett, Jr. et al. | |
| 7,754,852 B2 | 7/2010 | Burnett, Jr. et al. | |
| 7,803,901 B2 | 9/2010 | Burnett, Jr. et al. | |
| 7,964,564 B2 | 6/2011 | Burnett, Jr. et al. | |
| 8,063,191 B2 | 11/2011 | Burnett, Jr. et al. | |
| 8,283,318 B2 | 10/2012 | Chen et al. | |
| 8,324,162 B2 | 12/2012 | Simari et al. | |
| 2004/0086976 A1 | 5/2004 | Fleer et al. | |
| 2005/0059600 A1 | 3/2005 | Burnett, Jr. et al. | |
| 2011/0152191 A1 | 6/2011 | Burnett, Jr. et al. | |
| 2011/0152194 A1 | 6/2011 | Burnett, Jr. et al. | |
| 2011/0282030 A1 | 11/2011 | Dickey et al. | |
| 2012/0053123 A1 | 3/2012 | Burnett, Jr. et al. | |
| 2012/0108514 A1 | 5/2012 | Burnett, Jr. et al. | |

FOREIGN PATENT DOCUMENTS

| | | |
|---|---|---|
| EP | 45665 B1 | 9/1985 |
| EP | 0533084 * | 3/1993 |
| WO | WO9912576 * | 3/1999 |
| WO | WO2007034498 * | 3/2007 |

OTHER PUBLICATIONS

Barber et al., Atrial Natriuretic Peptide Preserves Endothelial Function during Intimal Hyperplasia, J. Vasc. Res., 42, 101-110, 2005.*
International Search Report and Written Opinion in International Application No. PCT/US2009/069687, mailed Sep. 2, 2010, 10 pages.
International Preliminary Report on Patentability in International Application No. PCT/US2009/069687, mailed Jul. 7, 2011, 6 pages.
Almquist et al., "Synthesis and biological activity of a ketomethylene analogue of a tripeptide inhibitor of angiotensin converting enzyme," *J. Med. Chem.*, 1980, 23:1392.
Banga, "Theme section: Transdermal delivery of proteins," *Pharm. Res.*, 2007, 24:1357-1359.
Barber et al, "Atrial natriuretic peptide preserves endothelial function during intimal hyperplasia," *J. Vasc. Res.*, 2005, 42:101-110.
Cataliotti et al., "Oral brain natriuretic peptide: A novel strategy for chronic protein therapy for cardiovascular disease," *Trends Cardiovasc. Med.*, 2007, 17:10-14.
US 6,884,780, Apr. 2005, Drammond et al., (withdrawn).
Chaurand et al., "Peptide and protein identification by matrix-assisted laser desorption ionization (MALDI) and MALDI-post-source decay time-of-flight mass spectrometry," *J. Am. Soc. Mass Spectrom.*, 1999, 10:91-103.
Cole et al., "The EBV-hybridoma technique and its application to human lung cancer," *Monoclonal Antibodies and Cancer Therapy*, Alan R. Liss, Inc. pp. 77-96, 1983.
Cote et al., "Generation of human monocolonal antibodies reactive with cellular antigens," *Proc. Natl. Acad. Sci. USA*, 1983, 80:2026-2030.
Dickey et al., "Novel bifunctional natriuretic peptide as potential therapeutics," *J. Biol. Chem.*, 2008, 283(50):35003-35009.
Gevaert et al., "Protein identification based on matrix assisted laser desorption/ionization-post source decay-mass spectrometry," *Electrophoresis*, 2001, 22:1645-1651.
Goebel and Neubert, "Dermal peptide using colloidal carrier systems," *Skin Pharmacol. Physiol.*, 2008, 21:3-9.
Guatelli et al., "Isothermal, in vitro amplification of nucleic acids by a multienzyme reaction modeled after retroviral replication," *Proc. Natl. Acad. Sci. USA*, 1990, 87:1874-1878.

(Continued)

Primary Examiner — Elly-Gerald Stoica
(74) *Attorney, Agent, or Firm* — Fish & Richardson P.C.

(57) ABSTRACT

Materials and methods related to using natriuretic polypeptides to reduce proliferation of smooth muscle cells, and to reduce or prevent restenosis.

2 Claims, 2 Drawing Sheets

OTHER PUBLICATIONS

Hann et al., "On the double bond isostere of the peptide bond: preparation of an enkephalin analogue," *J. Chem. Soc. Perkin Trans. 1*, 1982, 1:307-314.

Holladay et al., "Synthesis of hydroxyethylene and ketomethylene dipeptide isosteres," *Tetrahedron Lett.*, 1983, 24:4401-4404.

Hruby, "Conformational restrictions of biologically active peptides via amino acid side chain groups," *Life Sci.*, 1982, 31:189-199.

Hudson et al., "Methionine enkephalin and isosteric analogues I. Synthesis on a phenolic resin support," *Int. J. Pept. Prot. Res.*, 1979, 14:177-185.

Huse et al., "Generation of a Large combinatorial library of the immunoglobulin repertoire in phage lambda," *Science*, 1989, 246:1275.

Jennings-White et al., "Synthesis of ketomethylene analogs of dipeptides," *Tetrahedron Lett.*, 1982, 23:2533-2534.

Kohler et al., "Continuous cultures of fused cells secreting antibody of predefined specificity," *Nature*, 1975, 256:495.

Komatsu et al., "C-type natriuretic peptide (CNP) in rats and humans," *Endocrinol*, 1991, 129(2):1104-1106.

Kozbor et al., "The production of monoclonal antibodies from human lymphocytes," *Immunology Today*, 1983, 4(3):72-79.

Kuhn, "Structure, regulation, and function of mammalian membrane guanylyl cyclase receptors, with a focus on guanylyl cyclase-A," *Circ. Res.*, 2003, 93:700-709.

Lebl and Hruby, "Synthesis of cyclic peptides by solid phase methodology," *Tetrahedron Lett.*, 1984, 25:2067.

Lewis, "PCR's competitors are alive and well and moving rapidly towards commercialization," *Genetic Engineering News*, 1992, 12:1.

Lisy et al., "Design, synthesis and actions of a novel chimeric natriuretic peptide: CD-NP," *J. Am. Coll. Cardiol.*, 2008, 52(1):60-68.

Malik et al., "Recent advances in protein and peptide drug delivery systems," *Curr. Drug Deliv.*, 2007, 4:141-151.

Miller et al., "Amphiphilic conjugates of human brain natriuretic peptide designed for oral delivery: In vitro activity screening," *Bioconjugate Chem.*, 2006, 17:267-274.

Morley, "Modulation of the action of regulatory peptides by structural modification," *Trends Pharm. Sci.*, 1980, 463-468.

*PCR Primer: A Laboratory Manual*, ed. by Dieffenbach and Dveksler, Cold Spring Harbor Laboratory Press, 1995 (table of contents).

Prausnitz, "A peptide chaperone for transdermal drug delivery," *Nat. Biotechnol.*, 2006, 24(4):416-417.

Schiller et al., "A novel cyclic opioid peptide analog showing high preference for μ-receptors," *Biochem. Biophys. Res. Comm.*, 1985, 127:558-564.

Schiller et al., "Synthesis of side-chain to side-chain cyclized peptide analogs on solid supports," *Int. J. Peptide Protein Res.*, 1985, 25:171-177.

Schirger et al., "Vascular actions of brain natriuretic peptide: modulation by atherosclerosis and neutral endopeptidase inhibition," *J. Am. Coll. Cardiol.*, 2000, 35:796-801.

Spatola et al., "Structure-activity relationships of enkephalins containing serially replaced thiomethylene amide bond surrogates," *Life Sci.*, 1986, 38:1243-1249.

Spatola, "Peptide backbone modifications: A structure-activity analysis of peptides containing amide bond surrogates, conformational constraints, and Rela," *Chemistry and Biochemistry of Amino Acid Peptides and Proteins*, Chapter 5, B. Weinstein, ed., Marcel Dekker, New York, p. 267, (1983).

Tawaragi et al., "Gene and precursor structures of human C-type natriuretic peptide," *Biochem. Biophys. Res. Commun*, 1991, 175:645-651.

Veronese and Mero, "The impact of PEGylation on biological therapies," *BioDrugs*, 2008, 22:315-329.

Veronese and Pasut, "PEGylation, successful approach to drug delivery," *Drug Discov. Today*, 2005, 10:1451-1458.

Wang et al., "Albubnp, a recombinant B-type natriuretic peptide and human serum albumin fusion hormone, as a long-term therapy of congestive heart failure," *Pharm. Res.*, 2004, 21:2105-2111.

Weiss, "Hot prospect for new gene amplifier—ligase chain reaction, a combination DNA amplifier and genetic screen, could do for DNA diagnostics what PCR has done for basic molecular biology," *Science*, 1991, 254:1292.

Wermeling et al. "Microneedles permit transdermal delivery of a skin-impermeant medication to humans," *Proc. Natl. Acad. Sci. USA*, 2008, 105:2058-2063.

\* cited by examiner

SEQUENCE LISTING

```
<160> NUMBER OF SEQ ID NOS: 150

<210> SEQ ID NO 1
<211> LENGTH: 28
<212> TYPE: PRT
<213> ORGANISM: Homo sapiens

<400> SEQUENCE: 1

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 2
<211> LENGTH: 32
<212> TYPE: PRT
<213> ORGANISM: Homo sapiens

<400> SEQUENCE: 2

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 3
<211> LENGTH: 22
<212> TYPE: PRT
<213> ORGANISM: Homo sapiens

<400> SEQUENCE: 3

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 4
<211> LENGTH: 32
<212> TYPE: PRT
<213> ORGANISM: Homo sapiens

<400> SEQUENCE: 4

Thr Ala Pro Arg Ser Leu Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
```

```
                        20                  25                  30

<210> SEQ ID NO 5
<211> LENGTH: 38
<212> TYPE: PRT
<213> ORGANISM: Dendroaspis

<400> SEQUENCE: 5

Glu Val Lys Tyr Asp Pro Cys Phe Gly His Lys Ile Asp Arg Ile Asn
1               5                   10                  15

His Val Ser Asn Leu Gly Cys Pro Ser Leu Arg Asp Pro Arg Pro Asn
            20                  25                  30

Ala Pro Ser Thr Ser Ala
        35

<210> SEQ ID NO 6
<211> LENGTH: 26
<212> TYPE: PRT
<213> ORGANISM: Homo sapiens

<400> SEQUENCE: 6

Ser Pro Lys Met Val Gln Gly Ser Gly Cys Phe Gly Arg Lys Met Asp
1               5                   10                  15

Arg Ile Ser Ser Ser Ser Gly Leu Gly Cys
            20                  25

<210> SEQ ID NO 7
<211> LENGTH: 15
<212> TYPE: PRT
<213> ORGANISM: Dendroaspis

<400> SEQUENCE: 7

Pro Ser Leu Arg Asp Pro Arg Pro Asn Ala Pro Ser Thr Ser Ala
1               5                   10                  15

<210> SEQ ID NO 8
<211> LENGTH: 41
<212> TYPE: PRT
<213> ORGANISM: Artificial Sequence
<220> FEATURE:
<223> OTHER INFORMATION: synthetically generated polypeptide

<400> SEQUENCE: 8

Ser Pro Lys Met Val Gln Gly Ser Gly Cys Phe Gly Arg Lys Met Asp
1               5                   10                  15

Arg Ile Ser Ser Ser Ser Gly Leu Gly Cys Pro Ser Leu Arg Asp Pro
            20                  25                  30

Arg Pro Asn Ala Pro Ser Thr Ser Ala
        35                  40

<210> SEQ ID NO 9
<211> LENGTH: 37
<212> TYPE: PRT
<213> ORGANISM: Artificial Sequence
<220> FEATURE:
<223> OTHER INFORMATION: synthetically generated polypeptide

<400> SEQUENCE: 9

Gly Leu Ser Lys Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Ser Ala
        35
```

```
<210> SEQ ID NO 10
<211> LENGTH: 10
<212> TYPE: PRT
<213> ORGANISM: Homo sapiens

<400> SEQUENCE: 10

Thr Ala Pro Arg Ser Leu Arg Arg Ser Ser
1               5                   10

<210> SEQ ID NO 11
<211> LENGTH: 17
<212> TYPE: PRT
<213> ORGANISM: Homo sapiens

<400> SEQUENCE: 11

Cys Phe Gly Leu Lys Leu Asp Arg Ile Gly Ser Met Ser Gly Leu Gly
1               5                   10                  15

Cys

<210> SEQ ID NO 12
<211> LENGTH: 5
<212> TYPE: PRT
<213> ORGANISM: Homo sapiens

<400> SEQUENCE: 12

Asn Ser Phe Arg Tyr
1               5

<210> SEQ ID NO 13
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 13

Thr Ala Pro Arg Ser Leu Arg Arg Ser Ser Cys Phe Gly Leu Lys Leu
1               5                   10                  15

Asp Arg Ile Gly Ser Met Ser Gly Leu Gly Cys Asn Ser Phe Arg Tyr
                20                  25                  30

<210> SEQ ID NO 14
<211> LENGTH: 6
<212> TYPE: PRT
<213> ORGANISM: Homo sapiens

<400> SEQUENCE: 14

Ser Leu Arg Arg Ser Ser
1               5

<210> SEQ ID NO 15
<211> LENGTH: 17
<212> TYPE: PRT
<213> ORGANISM: Homo sapiens

<400> SEQUENCE: 15

Cys Phe Gly Arg Lys Met Asp Arg Ile Ser Ser Ser Ser Gly Leu Gly
1               5                   10                  15

Cys

<210> SEQ ID NO 16
<211> LENGTH: 28
```

<212> TYPE: PRT
<213> ORGANISM: Artificial Sequence
<220> FEATURE:
<223> OTHER INFORMATION: synthetically generated polypeptide

<400> SEQUENCE: 16

Ser Leu Arg Arg Ser Ser Cys Phe Gly Arg Lys Met Asp Arg Ile Ser
1               5                   10                  15
Ser Ser Ser Gly Leu Gly Cys Asn Ser Phe Arg Tyr
            20                  25

<210> SEQ ID NO 17
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 17

Thr Ala Pro Arg Ser Leu Arg Arg Ser Ser Cys Phe Gly Arg Lys Met
1               5                   10                  15
Asp Arg Ile Ser Ser Ser Ser Gly Leu Gly Cys Asn Ser Phe Arg Tyr
            20                  25                  30

<210> SEQ ID NO 18
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 18

Ser Leu Arg Arg Ser Ser Cys Phe Gly Leu Lys Leu Asp Arg Ile Gly
1               5                   10                  15
Ser Met Ser Gly Leu Gly Cys Asn Ser Phe Arg Tyr
            20                  25

<210> SEQ ID NO 19
<211> LENGTH: 6
<212> TYPE: PRT
<213> ORGANISM: Homo sapiens

<400> SEQUENCE: 19

Lys Val Leu Arg Arg His
1               5

<210> SEQ ID NO 20
<211> LENGTH: 29
<212> TYPE: PRT
<213> ORGANISM: Artificial Sequence
<220> FEATURE:
<223> OTHER INFORMATION: synthetically generated polypeptide

<400> SEQUENCE: 20

Ser Leu Arg Arg Ser Ser Cys Phe Gly Leu Lys Leu Asp Arg Ile Gly
1               5                   10                  15
Ser Met Ser Gly Leu Gly Cys Lys Val Leu Arg Arg His
            20                  25

<210> SEQ ID NO 21
<211> LENGTH: 9
<212> TYPE: PRT
<213> ORGANISM: Homo sapiens

<400> SEQUENCE: 21

-continued

```
Ser Pro Lys Met Val Gln Gly Ser Gly
1               5

<210> SEQ ID NO 22
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 22

Ser Pro Lys Met Val Gln Gly Ser Gly Cys Phe Gly Leu Lys Leu Asp
1               5                   10                  15

Arg Ile Gly Ser Met Ser Gly Leu Gly Cys Lys Val Leu Arg Arg His
            20                  25                  30

<210> SEQ ID NO 23
<211> LENGTH: 6
<212> TYPE: PRT
<213> ORGANISM: Dendroaspis

<400> SEQUENCE: 23

Glu Val Lys Tyr Asp Pro
1               5

<210> SEQ ID NO 24
<211> LENGTH: 38
<212> TYPE: PRT
<213> ORGANISM: Artificial Sequence
<220> FEATURE:
<223> OTHER INFORMATION: synthetically generated polypeptide

<400> SEQUENCE: 24

Glu Val Lys Tyr Asp Pro Cys Phe Gly Leu Lys Leu Asp Arg Ile Gly
1               5                   10                  15

Ser Met Ser Gly Leu Gly Cys Pro Ser Leu Arg Asp Pro Arg Pro Asn
            20                  25                  30

Ala Pro Ser Thr Ser Ala
        35

<210> SEQ ID NO 25
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 25

Thr Ala Pro Arg Ser Leu Arg Arg Ser Ser Cys Phe Gly Leu Lys Leu
1               5                   10                  15

Asp Arg Ile Gly Ser Met Ser Gly Leu Gly Cys Lys Val Leu Arg Arg
            20                  25                  30

His

<210> SEQ ID NO 26
<211> LENGTH: 5
<212> TYPE: PRT
<213> ORGANISM: Homo sapiens

<400> SEQUENCE: 26

Arg Met Asp Arg Ile
1               5

<210> SEQ ID NO 27
```

<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 27

Arg Met Asp Arg Ile Gly Leu Ser Lys Gly Cys Phe Gly Leu Lys Leu
1               5                   10                  15
Asp Arg Ile Gly Ser Met Ser Gly Leu Gly Cys Lys Val Leu Arg Arg
            20                  25                  30
His

<210> SEQ ID NO 28
<211> LENGTH: 22
<212> TYPE: PRT
<213> ORGANISM: Artificial Sequence
<220> FEATURE:
<223> OTHER INFORMATION: synthetically generated polypeptide

<400> SEQUENCE: 28

Gly Leu Ser Lys Gly Cys Phe Gly Leu Lys Leu Asp Arg Ile Arg Glu
1               5                   10                  15
Ala Ser Gly Leu Gly Cys
            20

<210> SEQ ID NO 29
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 29

Arg Met Asp Arg Ile Gly Leu Ser Lys Gly Cys Phe Gly Leu Lys Leu
1               5                   10                  15
Asp Arg Ile Arg Glu Ala Ser Gly Leu Gly Cys Lys Val Leu Arg Arg
            20                  25                  30
His

<210> SEQ ID NO 30
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 30

Gly Leu Ser Lys Gly Cys Phe Gly Leu Lys Leu Asp Arg Ile Arg Glu
1               5                   10                  15
Ala Ser Gly Leu Gly Cys Lys Val Leu Arg Arg His
            20                  25

<210> SEQ ID NO 31
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 31

Thr Leu Arg Arg Ser Ser Cys Phe Gly Gly Arg Met Asp Arg Ile Gly
1               5                   10                  15
Ala Gln Ser Gly Leu Gly Cys Asn Ser Phe Arg Tyr 20                  25

<210> SEQ ID NO 32
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 32

Ser Ile Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 33
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 33

Ser Leu Lys Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 34
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 34

Ser Leu Arg Lys Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 35
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 35

Ser Leu Arg Arg Ser Ser Cys Phe Gly Gly Arg Met Asp Arg Ile Gly
1               5                   10                  15

Ala Gln Ser Gly Leu Gly Cys Asn Thr Phe Arg Tyr
            20                  25

<210> SEQ ID NO 36
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 36

Ser Leu Arg Arg Ser Ser Cys Phe Gly Gly Arg Met Asp Arg Ile Gly
1               5                   10                  15

Ala Gln Ser Gly Leu Gly Cys Asn Ser Leu Arg Tyr 20                  25

<210> SEQ ID NO 37
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 37

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Lys Tyr
            20                  25

<210> SEQ ID NO 38
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 38

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Phe
            20                  25

<210> SEQ ID NO 39
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 39

Thr Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 40

Ser Gly Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 41

Ser Pro Arg Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His 20                  25                  30

<210> SEQ ID NO 42
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 42

Ser Pro Lys Leu Val Gln Gly Ser Gly Cys Phe Gly Arg Lys Met Asp
 1               5                  10                  15

Arg Ile Ser Ser Ser Ser Gly Leu Gly Cys Lys Val Leu Arg Arg His
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 43

Ser Pro Lys Met Val Gln Gly Ser Gly Cys Phe Gly Arg Lys Met Asp
 1               5                  10                  15

Arg Ile Ser Ser Ser Ser Gly Leu Gly Cys Lys Val Ile Arg Arg His
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 44

Ser Pro Lys Met Val Gln Gly Ser Gly Cys Phe Gly Arg Lys Met Asp
 1               5                  10                  15

Arg Ile Ser Ser Ser Ser Gly Leu Gly Cys Lys Val Leu Lys Arg His
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 45

Ser Pro Lys Met Val Gln Gly Ser Gly Cys Phe Gly Arg Lys Met Asp
 1               5                  10                  15

Arg Ile Ser Ser Ser Ser Gly Leu Gly Cys Lys Val Leu Arg Lys His
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 46

Ser Pro Lys Met Val Gln Gly Ser Gly Cys Phe Gly Arg Lys Met Asp
 1               5                  10                  15

Arg Ile Ser Ser Ser Ser Gly Leu Gly Cys Lys Val Leu Arg Arg Arg

<210> SEQ ID NO 47
<211> LENGTH: 22
<212> TYPE: PRT
<213> ORGANISM: Artificial Sequence
<220> FEATURE:
<223> OTHER INFORMATION: synthetically generated polypeptide

<400> SEQUENCE: 47

Pro Leu Ser Lys Gly Cys Phe Gly Leu Lys Leu Asp Arg Ile Gly Ser
1               5                   10                  15

Met Ser Gly Leu Gly Cys
            20

<210> SEQ ID NO 48
<211> LENGTH: 22
<212> TYPE: PRT
<213> ORGANISM: Artificial Sequence
<220> FEATURE:
<223> OTHER INFORMATION: synthetically generated polypeptide

<400> SEQUENCE: 48

Gly Ile Ser Lys Gly Cys Phe Gly Leu Lys Leu Asp Arg Ile Gly Ser
1               5                   10                  15

Met Ser Gly Leu Gly Cys
            20

<210> SEQ ID NO 49
<211> LENGTH: 22
<212> TYPE: PRT
<213> ORGANISM: Artificial Sequence
<220> FEATURE:
<223> OTHER INFORMATION: synthetically generated polypeptide

<400> SEQUENCE: 49

Gly Leu Thr Lys Gly Cys Phe Gly Leu Lys Leu Asp Arg Ile Gly Ser
1               5                   10                  15

Met Ser Gly Leu Gly Cys
            20

<210> SEQ ID NO 50
<211> LENGTH: 22
<212> TYPE: PRT
<213> ORGANISM: Artificial Sequence
<220> FEATURE:
<223> OTHER INFORMATION: synthetically generated polypeptide

<400> SEQUENCE: 50

Gly Leu Ser Arg Gly Cys Phe Gly Leu Lys Leu Asp Arg Ile Gly Ser
1               5                   10                  15

Met Ser Gly Leu Gly Cys
            20

<210> SEQ ID NO 51
<211> LENGTH: 22
<212> TYPE: PRT
<213> ORGANISM: Artificial Sequence
<220> FEATURE:
<223> OTHER INFORMATION: synthetically generated polypeptide

<400> SEQUENCE: 51

Gly Leu Ser Lys Gly Cys Phe Gly Leu Lys Leu Asp Arg Ile Gly Ser
1               5                   10                  15

Met Ser Pro Leu Gly Cys

```
                               20

<210> SEQ ID NO 52
<211> LENGTH: 22
<212> TYPE: PRT
<213> ORGANISM: Artificial Sequence
<220> FEATURE:
<223> OTHER INFORMATION: synthetically generated polypeptide

<400> SEQUENCE: 52

Gly Leu Ser Lys Gly Cys Phe Gly Leu Lys Leu Asp Arg Ile Gly Ser
 1               5                  10                  15

Met Ser Gly Ile Gly Cys
             20

<210> SEQ ID NO 53
<211> LENGTH: 22
<212> TYPE: PRT
<213> ORGANISM: Artificial Sequence
<220> FEATURE:
<223> OTHER INFORMATION: synthetically generated polypeptide

<400> SEQUENCE: 53

Gly Leu Ser Lys Gly Cys Phe Gly Leu Lys Leu Asp Arg Ile Gly Ser
 1               5                  10                  15

Met Ser Gly Leu Pro Cys
             20

<210> SEQ ID NO 54
<211> LENGTH: 22
<212> TYPE: PRT
<213> ORGANISM: Artificial Sequence
<220> FEATURE:
<223> OTHER INFORMATION: synthetically generated polypeptide

<400> SEQUENCE: 54

Gly Leu Ser Lys Gly Cys Phe Gly Leu Lys Leu Asp Arg Ile Gly Ser
 1               5                  10                  15

Met Ser Gly Leu Gly Ser
             20

<210> SEQ ID NO 55
<211> LENGTH: 41
<212> TYPE: PRT
<213> ORGANISM: Artificial Sequence
<220> FEATURE:
<223> OTHER INFORMATION: synthetically generated polypeptide

<400> SEQUENCE: 55

Thr Pro Lys Met Val Gln Gly Ser Gly Cys Phe Gly Arg Lys Met Asp
 1               5                  10                  15

Arg Ile Ser Ser Ser Ser Gly Leu Gly Cys Pro Ser Leu Arg Asp Pro
                20                  25                  30

Arg Pro Asn Ala Pro Ser Thr Ser Ala
             35                  40

<210> SEQ ID NO 56
<211> LENGTH: 41
<212> TYPE: PRT
<213> ORGANISM: Artificial Sequence
<220> FEATURE:
<223> OTHER INFORMATION: synthetically generated polypeptide

<400> SEQUENCE: 56

Ser Gly Lys Met Val Gln Gly Ser Gly Cys Phe Gly Arg Lys Met Asp
```

-continued

```
                1               5                  10                 15
Arg Ile Ser Ser Ser Ser Gly Leu Gly Cys Pro Ser Leu Arg Asp Pro
                20                 25                 30

Arg Pro Asn Ala Pro Ser Thr Ser Ala
            35                  40

<210> SEQ ID NO 57
<211> LENGTH: 41
<212> TYPE: PRT
<213> ORGANISM: Artificial Sequence
<220> FEATURE:
<223> OTHER INFORMATION: synthetically generated polypeptide

<400> SEQUENCE: 57

Ser Pro Arg Met Val Gln Gly Ser Gly Cys Phe Gly Arg Lys Met Asp
1               5                  10                 15

Arg Ile Ser Ser Ser Ser Gly Leu Gly Cys Pro Ser Leu Arg Asp Pro
                20                 25                 30

Arg Pro Asn Ala Pro Ser Thr Ser Ala
            35                  40

<210> SEQ ID NO 58
<211> LENGTH: 41
<212> TYPE: PRT
<213> ORGANISM: Artificial Sequence
<220> FEATURE:
<223> OTHER INFORMATION: synthetically generated polypeptide

<400> SEQUENCE: 58

Ser Pro Lys Leu Val Gln Gly Ser Gly Cys Phe Gly Arg Lys Met Asp
1               5                  10                 15

Arg Ile Ser Ser Ser Ser Gly Leu Gly Cys Pro Ser Leu Arg Asp Pro
                20                 25                 30

Arg Pro Asn Ala Pro Ser Thr Ser Ala
            35                  40

<210> SEQ ID NO 59
<211> LENGTH: 41
<212> TYPE: PRT
<213> ORGANISM: Artificial Sequence
<220> FEATURE:
<223> OTHER INFORMATION: synthetically generated polypeptide

<400> SEQUENCE: 59

Ser Pro Lys Met Val Gln Gly Ser Gly Cys Phe Gly Arg Lys Met Asp
1               5                  10                 15

Arg Ile Ser Ser Ser Ser Gly Leu Gly Cys Pro Ser Leu Arg Asp Pro
                20                 25                 30

Arg Pro Asn Ala Pro Thr Thr Ser Ala
            35                  40

<210> SEQ ID NO 60
<211> LENGTH: 41
<212> TYPE: PRT
<213> ORGANISM: Artificial Sequence
<220> FEATURE:
<223> OTHER INFORMATION: synthetically generated polypeptide

<400> SEQUENCE: 60

Ser Pro Lys Met Val Gln Gly Ser Gly Cys Phe Gly Arg Lys Met Asp
1               5                  10                 15

Arg Ile Ser Ser Ser Ser Gly Leu Gly Cys Pro Ser Leu Arg Asp Pro
                20                 25                 30
```

Arg Pro Asn Ala Pro Ser Ser Ser Ala
        35                  40

<210> SEQ ID NO 61
<211> LENGTH: 41
<212> TYPE: PRT
<213> ORGANISM: Artificial Sequence
<220> FEATURE:
<223> OTHER INFORMATION: synthetically generated polypeptide

<400> SEQUENCE: 61

Ser Pro Lys Met Val Gln Gly Ser Gly Cys Phe Gly Arg Lys Met Asp
 1               5                  10                  15

Arg Ile Ser Ser Ser Gly Leu Gly Cys Pro Ser Leu Arg Asp Pro
            20                  25                  30

Arg Pro Asn Ala Pro Ser Thr Thr Ala
        35                  40

<210> SEQ ID NO 62
<211> LENGTH: 41
<212> TYPE: PRT
<213> ORGANISM: Artificial Sequence
<220> FEATURE:
<223> OTHER INFORMATION: synthetically generated polypeptide

<400> SEQUENCE: 62

Ser Pro Lys Met Val Gln Gly Ser Gly Cys Phe Gly Arg Lys Met Asp
 1               5                  10                  15

Arg Ile Ser Ser Ser Gly Leu Gly Cys Pro Ser Leu Arg Asp Pro
            20                  25                  30

Arg Pro Asn Ala Pro Ser Thr Ser Val
        35                  40

<210> SEQ ID NO 63
<211> LENGTH: 37
<212> TYPE: PRT
<213> ORGANISM: Artificial Sequence
<220> FEATURE:
<223> OTHER INFORMATION: synthetically generated polypeptide

<400> SEQUENCE: 63

Pro Leu Ser Lys Gly Cys Phe Gly Leu Lys Leu Asp Arg Ile Gly Ser
 1               5                  10                  15

Met Ser Gly Leu Gly Cys Pro Ser Leu Arg Asp Pro Arg Pro Asn Ala
            20                  25                  30

Pro Ser Thr Ser Ala
        35

<210> SEQ ID NO 64
<211> LENGTH: 37
<212> TYPE: PRT
<213> ORGANISM: Artificial Sequence
<220> FEATURE:
<223> OTHER INFORMATION: synthetically generated polypeptide

<400> SEQUENCE: 64

Gly Ile Ser Lys Gly Cys Phe Gly Leu Lys Leu Asp Arg Ile Gly Ser
 1               5                  10                  15

Met Ser Gly Leu Gly Cys Pro Ser Leu Arg Asp Pro Arg Pro Asn Ala
            20                  25                  30

Pro Ser Thr Ser Ala
        35

<210> SEQ ID NO 65
<211> LENGTH: 37
<212> TYPE: PRT
<213> ORGANISM: Artificial Sequence
<220> FEATURE:
<223> OTHER INFORMATION: synthetically generated polypeptide

<400> SEQUENCE: 65

Gly Leu Thr Lys Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Ser Ala
        35

<210> SEQ ID NO 66
<211> LENGTH: 37
<212> TYPE: PRT
<213> ORGANISM: Artificial Sequence
<220> FEATURE:
<223> OTHER INFORMATION: synthetically generated polypeptide

<400> SEQUENCE: 66

Gly Leu Ser Arg Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Ser Ala
        35

<210> SEQ ID NO 67
<211> LENGTH: 37
<212> TYPE: PRT
<213> ORGANISM: Artificial Sequence
<220> FEATURE:
<223> OTHER INFORMATION: synthetically generated polypeptide

<400> SEQUENCE: 67

Gly Leu Ser Lys Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Thr Thr Ser Ala
        35

<210> SEQ ID NO 68
<211> LENGTH: 37
<212> TYPE: PRT
<213> ORGANISM: Artificial Sequence
<220> FEATURE:
<223> OTHER INFORMATION: synthetically generated polypeptide

<400> SEQUENCE: 68

Gly Leu Ser Lys Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Ser Ser Ala
        35

<210> SEQ ID NO 69
<211> LENGTH: 37
<212> TYPE: PRT

<213> ORGANISM: Artificial Sequence
<220> FEATURE:
<223> OTHER INFORMATION: synthetically generated polypeptide

<400> SEQUENCE: 69

Gly Leu Ser Lys Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Thr Ala
        35

<210> SEQ ID NO 70
<211> LENGTH: 37
<212> TYPE: PRT
<213> ORGANISM: Artificial Sequence
<220> FEATURE:
<223> OTHER INFORMATION: synthetically generated polypeptide

<400> SEQUENCE: 70

Gly Leu Ser Lys Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Ser Val
        35

<210> SEQ ID NO 71
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 71

Ser Ala Pro Arg Ser Leu Arg Arg Ser Ser Cys Phe Gly Leu Lys Leu
1               5                   10                  15

Asp Arg Ile Gly Ser Met Ser Gly Leu Gly Cys Asn Ser Phe Arg Tyr
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 72

Thr Val Pro Arg Ser Leu Arg Arg Ser Ser Cys Phe Gly Leu Lys Leu
1               5                   10                  15

Asp Arg Ile Gly Ser Met Ser Gly Leu Gly Cys Asn Ser Phe Arg Tyr
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 73

Thr Ala Gly Arg Ser Leu Arg Arg Ser Ser Cys Phe Gly Leu Lys Leu
1               5                   10                  15

Asp Arg Ile Gly Ser Met Ser Gly Leu Gly Cys Asn Ser Phe Arg Tyr 20                  25                  30

<210> SEQ ID NO 74
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 74

Thr Ala Pro Lys Ser Leu Arg Arg Ser Ser Cys Phe Gly Leu Lys Leu
1               5                   10                  15

Asp Arg Ile Gly Ser Met Ser Gly Leu Gly Cys Asn Ser Phe Arg Tyr
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 75

Thr Ala Pro Arg Ser Leu Arg Arg Ser Ser Cys Phe Gly Leu Lys Leu
1               5                   10                  15

Asp Arg Ile Gly Ser Met Ser Gly Leu Gly Cys Asn Thr Phe Arg Tyr
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 76

Thr Ala Pro Arg Ser Leu Arg Arg Ser Ser Cys Phe Gly Leu Lys Leu
1               5                   10                  15

Asp Arg Ile Gly Ser Met Ser Gly Leu Gly Cys Asn Ser Leu Arg Tyr
            20                  25                  30

<210> SEQ ID NO 77
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 77

Thr Ala Pro Arg Ser Leu Arg Arg Ser Ser Cys Phe Gly Leu Lys Leu
1               5                   10                  15

Asp Arg Ile Gly Ser Met Ser Gly Leu Gly Cys Asn Ser Phe Lys Tyr
            20                  25                  30

<210> SEQ ID NO 78
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 78

Thr Ala Pro Arg Ser Leu Arg Arg Ser Ser Cys Phe Gly Leu Lys Leu
1               5                   10                  15

Asp Arg Ile Gly Ser Met Ser Gly Leu Gly Cys Asn Ser Phe Arg Phe

```
                  20                  25                  30
```

<210> SEQ ID NO 79
<211> LENGTH: 28
<212> TYPE: PRT
<213> ORGANISM: Artificial Sequence
<220> FEATURE:
<223> OTHER INFORMATION: synthetically generated polypeptide
<400> SEQUENCE: 79

```
Thr Leu Arg Arg Ser Ser Cys Phe Gly Arg Lys Met Asp Arg Ile Ser
1               5                   10                  15

Ser Ser Ser Gly Leu Gly Cys Asn Ser Phe Arg Tyr
            20                  25
```

<210> SEQ ID NO 80
<211> LENGTH: 28
<212> TYPE: PRT
<213> ORGANISM: Artificial Sequence
<220> FEATURE:
<223> OTHER INFORMATION: synthetically generated polypeptide
<400> SEQUENCE: 80

```
Ser Ile Arg Arg Ser Ser Cys Phe Gly Arg Lys Met Asp Arg Ile Ser
1               5                   10                  15

Ser Ser Ser Gly Leu Gly Cys Asn Ser Phe Arg Tyr
            20                  25
```

<210> SEQ ID NO 81
<211> LENGTH: 28
<212> TYPE: PRT
<213> ORGANISM: Artificial Sequence
<220> FEATURE:
<223> OTHER INFORMATION: synthetically generated polypeptide
<400> SEQUENCE: 81

```
Ser Leu Lys Arg Ser Ser Cys Phe Gly Arg Lys Met Asp Arg Ile Ser
1               5                   10                  15

Ser Ser Ser Gly Leu Gly Cys Asn Ser Phe Arg Tyr
            20                  25
```

<210> SEQ ID NO 82
<211> LENGTH: 28
<212> TYPE: PRT
<213> ORGANISM: Artificial Sequence
<220> FEATURE:
<223> OTHER INFORMATION: synthetically generated polypeptide
<400> SEQUENCE: 82

```
Ser Leu Arg Lys Ser Ser Cys Phe Gly Arg Lys Met Asp Arg Ile Ser
1               5                   10                  15

Ser Ser Ser Gly Leu Gly Cys Asn Ser Phe Arg Tyr
            20                  25
```

<210> SEQ ID NO 83
<211> LENGTH: 28
<212> TYPE: PRT
<213> ORGANISM: Artificial Sequence
<220> FEATURE:
<223> OTHER INFORMATION: synthetically generated polypeptide
<400> SEQUENCE: 83

```
Ser Leu Arg Arg Ser Ser Cys Phe Gly Arg Lys Met Asp Arg Ile Ser
1               5                   10                  15

Ser Ser Ser Gly Leu Gly Cys Asn Thr Phe Arg Tyr
```

20              25

<210> SEQ ID NO 84
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 84

Ser Leu Arg Arg Ser Ser Cys Phe Gly Arg Lys Met Asp Arg Ile Ser
1               5                   10                  15

Ser Ser Ser Gly Leu Gly Cys Asn Ser Leu Arg Tyr
            20                  25

<210> SEQ ID NO 85
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 85

Ser Leu Arg Arg Ser Ser Cys Phe Gly Arg Lys Met Asp Arg Ile Ser
1               5                   10                  15

Ser Ser Ser Gly Leu Gly Cys Asn Ser Phe Lys Tyr
            20                  25

<210> SEQ ID NO 86
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 86

Ser Leu Arg Arg Ser Ser Cys Phe Gly Arg Lys Met Asp Arg Ile Ser
1               5                   10                  15

Ser Ser Ser Gly Leu Gly Cys Asn Ser Phe Arg Phe
            20                  25

<210> SEQ ID NO 87
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 87

Ser Ala Pro Arg Ser Leu Arg Arg Ser Ser Cys Phe Gly Arg Lys Met
1               5                   10                  15

Asp Arg Ile Ser Ser Ser Ser Gly Leu Gly Cys Asn Ser Phe Arg Tyr
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 88

Thr Val Pro Arg Ser Leu Arg Arg Ser Ser Cys Phe Gly Arg Lys Met
1               5                   10                  15

Asp Arg Ile Ser Ser Ser Ser Gly Leu Gly Cys Asn Ser Phe Arg Tyr

<210> SEQ ID NO 89
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 89

Thr Ala Gly Arg Ser Leu Arg Arg Ser Ser Cys Phe Gly Arg Lys Met
1               5                   10                  15

Asp Arg Ile Ser Ser Ser Ser Gly Leu Gly Cys Asn Ser Phe Arg Tyr
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 90

Thr Ala Pro Lys Ser Leu Arg Arg Ser Ser Cys Phe Gly Arg Lys Met
1               5                   10                  15

Asp Arg Ile Ser Ser Ser Ser Gly Leu Gly Cys Asn Ser Phe Arg Tyr
            20                  25                  30

<210> SEQ ID NO 91
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 91

Thr Ala Pro Arg Ser Leu Arg Arg Ser Ser Cys Phe Gly Arg Lys Met
1               5                   10                  15

Asp Arg Ile Ser Ser Ser Ser Gly Leu Gly Cys Asn Thr Phe Arg Tyr
            20                  25                  30

<210> SEQ ID NO 92
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 92

Thr Ala Pro Arg Ser Leu Arg Arg Ser Ser Cys Phe Gly Arg Lys Met
1               5                   10                  15

Asp Arg Ile Ser Ser Ser Ser Gly Leu Gly Cys Asn Ser Leu Arg Tyr
            20                  25                  30

<210> SEQ ID NO 93
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 93

Thr Ala Pro Arg Ser Leu Arg Arg Ser Ser Cys Phe Gly Arg Lys Met
1               5                   10                  15

Asp Arg Ile Ser Ser Ser Ser Gly Leu Gly Cys Asn Ser Phe Lys Tyr

<210> SEQ ID NO 94
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 94

Thr Ala Pro Arg Ser Leu Arg Arg Ser Ser Cys Phe Gly Arg Lys Met
 1               5                  10                  15

Asp Arg Ile Ser Ser Ser Ser Gly Leu Gly Cys Asn Ser Phe Arg Phe
            20                  25                  30

<210> SEQ ID NO 95
<211> LENGTH: 29
<212> TYPE: PRT
<213> ORGANISM: Artificial Sequence
<220> FEATURE:
<223> OTHER INFORMATION: synthetically generated polypeptide

<400> SEQUENCE: 95

Thr Leu Arg Arg Ser Ser Cys Phe Gly Leu Lys Leu Asp Arg Ile Gly
 1               5                  10                  15

Ser Met Ser Gly Leu Gly Cys Lys Val Leu Arg Arg His
            20                  25

<210> SEQ ID NO 96
<211> LENGTH: 29
<212> TYPE: PRT
<213> ORGANISM: Artificial Sequence
<220> FEATURE:
<223> OTHER INFORMATION: synthetically generated polypeptide

<400> SEQUENCE: 96

Ser Ile Arg Arg Ser Ser Cys Phe Gly Leu Lys Leu Asp Arg Ile Gly
 1               5                  10                  15

Ser Met Ser Gly Leu Gly Cys Lys Val Leu Arg Arg His
            20                  25

<210> SEQ ID NO 97
<211> LENGTH: 29
<212> TYPE: PRT
<213> ORGANISM: Artificial Sequence
<220> FEATURE:
<223> OTHER INFORMATION: synthetically generated polypeptide

<400> SEQUENCE: 97

Ser Leu Lys Arg Ser Ser Cys Phe Gly Leu Lys Leu Asp Arg Ile Gly
 1               5                  10                  15

Ser Met Ser Gly Leu Gly Cys Lys Val Leu Arg Arg His
            20                  25

<210> SEQ ID NO 98
<211> LENGTH: 29
<212> TYPE: PRT
<213> ORGANISM: Artificial Sequence
<220> FEATURE:
<223> OTHER INFORMATION: synthetically generated polypeptide

<400> SEQUENCE: 98

Ser Leu Arg Lys Ser Ser Cys Phe Gly Leu Lys Leu Asp Arg Ile Gly
 1               5                  10                  15

Ser Met Ser Gly Leu Gly Cys Lys Val Leu Arg Arg His

```
            20                  25

<210> SEQ ID NO 99
<211> LENGTH: 29
<212> TYPE: PRT
<213> ORGANISM: Artificial Sequence
<220> FEATURE:
<223> OTHER INFORMATION: synthetically generated polypeptide

<400> SEQUENCE: 99

Ser Leu Arg Arg Ser Ser Cys Phe Gly Leu Lys Leu Asp Arg Ile Gly
1               5                   10                  15

Ser Met Ser Gly Leu Gly Cys Lys Val Ile Arg Arg His
            20                  25

<210> SEQ ID NO 100
<211> LENGTH: 29
<212> TYPE: PRT
<213> ORGANISM: Artificial Sequence
<220> FEATURE:
<223> OTHER INFORMATION: synthetically generated polypeptide

<400> SEQUENCE: 100

Ser Leu Arg Arg Ser Ser Cys Phe Gly Leu Lys Leu Asp Arg Ile Gly
1               5                   10                  15

Ser Met Ser Gly Leu Gly Cys Lys Val Leu Lys Arg His
            20                  25

<210> SEQ ID NO 101
<211> LENGTH: 29
<212> TYPE: PRT
<213> ORGANISM: Artificial Sequence
<220> FEATURE:
<223> OTHER INFORMATION: synthetically generated polypeptide

<400> SEQUENCE: 101

Ser Leu Arg Arg Ser Ser Cys Phe Gly Leu Lys Leu Asp Arg Ile Gly
1               5                   10                  15

Ser Met Ser Gly Leu Gly Cys Lys Val Leu Arg Lys His
            20                  25

<210> SEQ ID NO 102
<211> LENGTH: 29
<212> TYPE: PRT
<213> ORGANISM: Artificial Sequence
<220> FEATURE:
<223> OTHER INFORMATION: synthetically generated polypeptide

<400> SEQUENCE: 102

Ser Leu Arg Arg Ser Ser Cys Phe Gly Leu Lys Leu Asp Arg Ile Gly
1               5                   10                  15

Ser Met Ser Gly Leu Gly Cys Lys Val Leu Arg Arg Arg
            20                  25

<210> SEQ ID NO 103
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 103

Thr Pro Lys Met Val Gln Gly Ser Gly Cys Phe Gly Leu Lys Leu Asp
1               5                   10                  15

Arg Ile Gly Ser Met Ser Gly Leu Gly Cys Lys Val Leu Arg Arg His
```

20          25          30

<210> SEQ ID NO 104
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 104

Ser Gly Lys Met Val Gln Gly Ser Gly Cys Phe Gly Leu Lys Leu Asp
1               5                   10                  15

Arg Ile Gly Ser Met Ser Gly Leu Gly Cys Lys Val Leu Arg Arg His
            20                  25                  30

<210> SEQ ID NO 105
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 105

Ser Pro Arg Met Val Gln Gly Ser Gly Cys Phe Gly Leu Lys Leu Asp
1               5                   10                  15

Arg Ile Gly Ser Met Ser Gly Leu Gly Cys Lys Val Leu Arg Arg His
            20                  25                  30

<210> SEQ ID NO 106
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 106

Ser Pro Lys Leu Val Gln Gly Ser Gly Cys Phe Gly Leu Lys Leu Asp
1               5                   10                  15

Arg Ile Gly Ser Met Ser Gly Leu Gly Cys Lys Val Leu Arg Arg His
            20                  25                  30

<210> SEQ ID NO 107
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 107

Ser Pro Lys Met Val Gln Gly Ser Gly Cys Phe Gly Leu Lys Leu Asp
1               5                   10                  15

Arg Ile Gly Ser Met Ser Gly Leu Gly Cys Lys Val Ile Arg Arg His
            20                  25                  30

<210> SEQ ID NO 108
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 108

Ser Pro Lys Met Val Gln Gly Ser Gly Cys Phe Gly Leu Lys Leu Asp
1               5                   10                  15

Arg Ile Gly Ser Met Ser Gly Leu Gly Cys Lys Val Leu Lys Arg His

<210> SEQ ID NO 109
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 109

Ser Pro Lys Met Val Gln Gly Ser Gly Cys Phe Gly Leu Lys Leu Asp
1               5                   10                  15
Arg Ile Gly Ser Met Ser Gly Leu Gly Cys Lys Val Leu Arg Lys His
            20                  25                  30

<210> SEQ ID NO 110
<211> LENGTH: 32
<212> TYPE: PRT
<213> ORGANISM: Artificial Sequence
<220> FEATURE:
<223> OTHER INFORMATION: synthetically generated polypeptide

<400> SEQUENCE: 110

Ser Pro Lys Met Val Gln Gly Ser Gly Cys Phe Gly Leu Lys Leu Asp
1               5                   10                  15
Arg Ile Gly Ser Met Ser Gly Leu Gly Cys Lys Val Leu Arg Arg Arg
            20                  25                  30

<210> SEQ ID NO 111
<211> LENGTH: 38
<212> TYPE: PRT
<213> ORGANISM: Artificial Sequence
<220> FEATURE:
<223> OTHER INFORMATION: synthetically generated polypeptide

<400> SEQUENCE: 111

Asp Val Lys Tyr Asp Pro Cys Phe Gly Leu Lys Leu Asp Arg Ile Gly
1               5                   10                  15
Ser Met Ser Gly Leu Gly Cys Pro Ser Leu Arg Asp Pro Arg Pro Asn
            20                  25                  30
Ala Pro Ser Thr Ser Ala
        35

<210> SEQ ID NO 112
<211> LENGTH: 38
<212> TYPE: PRT
<213> ORGANISM: Artificial Sequence
<220> FEATURE:
<223> OTHER INFORMATION: synthetically generated polypeptide

<400> SEQUENCE: 112

Glu Leu Lys Tyr Asp Pro Cys Phe Gly Leu Lys Leu Asp Arg Ile Gly
1               5                   10                  15
Ser Met Ser Gly Leu Gly Cys Pro Ser Leu Arg Asp Pro Arg Pro Asn
            20                  25                  30
Ala Pro Ser Thr Ser Ala
        35

<210> SEQ ID NO 113
<211> LENGTH: 38
<212> TYPE: PRT
<213> ORGANISM: Artificial Sequence
<220> FEATURE:
<223> OTHER INFORMATION: synthetically generated polypeptide

```
<400> SEQUENCE: 113

Glu Val Arg Tyr Asp Pro Cys Phe Gly Leu Lys Leu Asp Arg Ile Gly
1               5                   10                  15

Ser Met Ser Gly Leu Gly Cys Pro Ser Leu Arg Asp Pro Arg Pro Asn
            20                  25                  30

Ala Pro Ser Thr Ser Ala
        35

<210> SEQ ID NO 114
<211> LENGTH: 38
<212> TYPE: PRT
<213> ORGANISM: Artificial Sequence
<220> FEATURE:
<223> OTHER INFORMATION: synthetically generated polypeptide

<400> SEQUENCE: 114

Glu Val Lys Phe Asp Pro Cys Phe Gly Leu Lys Leu Asp Arg Ile Gly
1               5                   10                  15

Ser Met Ser Gly Leu Gly Cys Pro Ser Leu Arg Asp Pro Arg Pro Asn
            20                  25                  30

Ala Pro Ser Thr Ser Ala
        35

<210> SEQ ID NO 115
<211> LENGTH: 38
<212> TYPE: PRT
<213> ORGANISM: Artificial Sequence
<220> FEATURE:
<223> OTHER INFORMATION: synthetically generated polypeptide

<400> SEQUENCE: 115

Glu Val Lys Tyr Asp Pro Cys Phe Gly Leu Lys Leu Asp Arg Ile Gly
1               5                   10                  15

Ser Met Ser Gly Leu Gly Cys Pro Ser Leu Arg Asp Pro Arg Pro Asn
            20                  25                  30

Ala Pro Thr Thr Ser Ala
        35

<210> SEQ ID NO 116
<211> LENGTH: 38
<212> TYPE: PRT
<213> ORGANISM: Artificial Sequence
<220> FEATURE:
<223> OTHER INFORMATION: synthetically generated polypeptide

<400> SEQUENCE: 116

Glu Val Lys Tyr Asp Pro Cys Phe Gly Leu Lys Leu Asp Arg Ile Gly
1               5                   10                  15

Ser Met Ser Gly Leu Gly Cys Pro Ser Leu Arg Asp Pro Arg Pro Asn
            20                  25                  30

Ala Pro Ser Ser Ser Ala
        35

<210> SEQ ID NO 117
<211> LENGTH: 38
<212> TYPE: PRT
<213> ORGANISM: Artificial Sequence
<220> FEATURE:
<223> OTHER INFORMATION: synthetically generated polypeptide

<400> SEQUENCE: 117

Glu Val Lys Tyr Asp Pro Cys Phe Gly Leu Lys Leu Asp Arg Ile Gly
1               5                   10                  15
```

```
Ser Met Ser Gly Leu Gly Cys Pro Ser Leu Arg Asp Pro Arg Pro Asn
            20                  25                  30

Ala Pro Ser Thr Thr Ala
            35
```

<210> SEQ ID NO 118
<211> LENGTH: 38
<212> TYPE: PRT
<213> ORGANISM: Artificial Sequence
<220> FEATURE:
<223> OTHER INFORMATION: synthetically generated polypeptide

<400> SEQUENCE: 118

```
Glu Val Lys Tyr Asp Pro Cys Phe Gly Leu Lys Leu Asp Arg Ile Gly
 1               5                  10                  15

Ser Met Ser Gly Leu Gly Cys Pro Ser Leu Arg Asp Pro Arg Pro Asn
            20                  25                  30

Ala Pro Ser Thr Ser Val
            35
```

<210> SEQ ID NO 119
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 119

```
Ser Ala Pro Arg Ser Leu Arg Arg Ser Ser Cys Phe Gly Leu Lys Leu
 1               5                  10                  15

Asp Arg Ile Gly Ser Met Ser Gly Leu Gly Cys Lys Val Leu Arg Arg
            20                  25                  30

His
```

<210> SEQ ID NO 120
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 120

```
Thr Val Pro Arg Ser Leu Arg Arg Ser Ser Cys Phe Gly Leu Lys Leu
 1               5                  10                  15

Asp Arg Ile Gly Ser Met Ser Gly Leu Gly Cys Lys Val Leu Arg Arg
            20                  25                  30

His
```

<210> SEQ ID NO 121
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 121

```
Thr Ala Gly Arg Ser Leu Arg Arg Ser Ser Cys Phe Gly Leu Lys Leu
 1               5                  10                  15

Asp Arg Ile Gly Ser Met Ser Gly Leu Gly Cys Lys Val Leu Arg Arg
            20                  25                  30

His
```

<210> SEQ ID NO 122
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 122

Thr Ala Pro Lys Ser Leu Arg Arg Ser Ser Cys Phe Gly Leu Lys Leu
1               5                   10                  15

Asp Arg Ile Gly Ser Met Ser Gly Leu Gly Cys Lys Val Leu Arg Arg
            20                  25                  30

His

<210> SEQ ID NO 123
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 123

Thr Ala Pro Arg Ser Leu Arg Arg Ser Ser Cys Phe Gly Leu Lys Leu
1               5                   10                  15

Asp Arg Ile Gly Ser Met Ser Gly Leu Gly Cys Lys Val Ile Arg Arg
            20                  25                  30

His

<210> SEQ ID NO 124
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 124

Thr Ala Pro Arg Ser Leu Arg Arg Ser Ser Cys Phe Gly Leu Lys Leu
1               5                   10                  15

Asp Arg Ile Gly Ser Met Ser Gly Leu Gly Cys Lys Val Leu Lys Arg
            20                  25                  30

His

<210> SEQ ID NO 125
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 125

Thr Ala Pro Arg Ser Leu Arg Arg Ser Ser Cys Phe Gly Leu Lys Leu
1               5                   10                  15

Asp Arg Ile Gly Ser Met Ser Gly Leu Gly Cys Lys Val Leu Arg Lys
            20                  25                  30

His

<210> SEQ ID NO 126
<211> LENGTH: 33
<212> TYPE: PRT
<213> ORGANISM: Artificial Sequence
<220> FEATURE:
<223> OTHER INFORMATION: synthetically generated polypeptide

```
<400> SEQUENCE: 126

Thr Ala Pro Arg Ser Leu Arg Arg Ser Ser Cys Phe Gly Leu Lys Leu
1               5                   10                  15
Asp Arg Ile Gly Ser Met Ser Gly Leu Gly Cys Lys Val Leu Arg Arg
            20                  25                  30
Arg

<210> SEQ ID NO 127
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 127

Lys Met Asp Arg Ile Gly Leu Ser Lys Gly Cys Phe Gly Leu Lys Leu
1               5                   10                  15
Asp Arg Ile Gly Ser Met Ser Gly Leu Gly Cys Lys Val Leu Arg Arg
            20                  25                  30
His

<210> SEQ ID NO 128
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 128

Arg Leu Asp Arg Ile Gly Leu Ser Lys Gly Cys Phe Gly Leu Lys Leu
1               5                   10                  15
Asp Arg Ile Gly Ser Met Ser Gly Leu Gly Cys Lys Val Leu Arg Arg
            20                  25                  30
His

<210> SEQ ID NO 129
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 129

Arg Met Glu Arg Ile Gly Leu Ser Lys Gly Cys Phe Gly Leu Lys Leu
1               5                   10                  15
Asp Arg Ile Gly Ser Met Ser Gly Leu Gly Cys Lys Val Leu Arg Arg
            20                  25                  30
His

<210> SEQ ID NO 130
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 130

Arg Met Asp Lys Ile Gly Leu Ser Lys Gly Cys Phe Gly Leu Lys Leu
1               5                   10                  15
Asp Arg Ile Gly Ser Met Ser Gly Leu Gly Cys Lys Val Leu Arg Arg
            20                  25                  30
```

His

<210> SEQ ID NO 131
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 131

Arg Met Asp Arg Ile Gly Leu Ser Lys Gly Cys Phe Gly Leu Lys Leu
 1               5                  10                  15

Asp Arg Ile Gly Ser Met Ser Gly Leu Gly Cys Lys Val Ile Arg Arg
            20                  25                  30

His

<210> SEQ ID NO 132
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 132

Arg Met Asp Arg Ile Gly Leu Ser Lys Gly Cys Phe Gly Leu Lys Leu
 1               5                  10                  15

Asp Arg Ile Gly Ser Met Ser Gly Leu Gly Cys Lys Val Leu Lys Arg
            20                  25                  30

His

<210> SEQ ID NO 133
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 133

Arg Met Asp Arg Ile Gly Leu Ser Lys Gly Cys Phe Gly Leu Lys Leu
 1               5                  10                  15

Asp Arg Ile Gly Ser Met Ser Gly Leu Gly Cys Lys Val Leu Arg Lys
            20                  25                  30

His

<210> SEQ ID NO 134
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 134

Arg Met Asp Arg Ile Gly Leu Ser Lys Gly Cys Phe Gly Leu Lys Leu
 1               5                  10                  15

Asp Arg Ile Gly Ser Met Ser Gly Leu Gly Cys Lys Val Leu Arg Arg
            20                  25                  30

Arg

<210> SEQ ID NO 135
<211> LENGTH: 33
<212> TYPE: PRT
<213> ORGANISM: Artificial Sequence
<220> FEATURE:

<223> OTHER INFORMATION: synthetically generated polypeptide

<400> SEQUENCE: 135

Lys Met Asp Arg Ile Gly Leu Ser Lys Gly Cys Phe Gly Leu Lys Leu
1               5                   10                  15

Asp Arg Ile Arg Glu Ala Ser Gly Leu Gly Cys Lys Val Leu Arg Arg
            20                  25                  30

His

<210> SEQ ID NO 136
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 136

Arg Leu Asp Arg Ile Gly Leu Ser Lys Gly Cys Phe Gly Leu Lys Leu
1               5                   10                  15

Asp Arg Ile Arg Glu Ala Ser Gly Leu Gly Cys Lys Val Leu Arg Arg
            20                  25                  30

His

<210> SEQ ID NO 137
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 137

Arg Met Glu Arg Ile Gly Leu Ser Lys Gly Cys Phe Gly Leu Lys Leu
1               5                   10                  15

Asp Arg Ile Arg Glu Ala Ser Gly Leu Gly Cys Lys Val Leu Arg Arg
            20                  25                  30

His

<210> SEQ ID NO 138
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 138

Arg Met Asp Lys Ile Gly Leu Ser Lys Gly Cys Phe Gly Leu Lys Leu
1               5                   10                  15

Asp Arg Ile Arg Glu Ala Ser Gly Leu Gly Cys Lys Val Leu Arg Arg
            20                  25                  30

His

<210> SEQ ID NO 139
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 139

Arg Met Asp Arg Ile Gly Leu Ser Lys Gly Cys Phe Gly Leu Lys Leu
1               5                   10                  15

Asp Arg Ile Arg Glu Ala Ser Gly Leu Gly Cys Lys Val Ile Arg Arg 20                  25                  30

His

<210> SEQ ID NO 140
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 140

Arg Met Asp Arg Ile Gly Leu Ser Lys Gly Cys Phe Gly Leu Lys Leu
 1               5                  10                  15

Asp Arg Ile Arg Glu Ala Ser Gly Leu Gly Cys Lys Val Leu Lys Arg
                20                  25                  30

His

<210> SEQ ID NO 141
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 141

Arg Met Asp Arg Ile Gly Leu Ser Lys Gly Cys Phe Gly Leu Lys Leu
 1               5                  10                  15

Asp Arg Ile Arg Glu Ala Ser Gly Leu Gly Cys Lys Val Leu Arg Lys
                20                  25                  30

His

<210> SEQ ID NO 142
<211> LENGTH: 33
<212> TYPE: PRT
<213> ORGANISM: Artificial Sequence
<220> FEATURE:
<223> OTHER INFORMATION: synthetically generated polypeptide

<400> SEQUENCE: 142

Arg Met Asp Arg Ile Gly Leu Ser Lys Gly Cys Phe Gly Leu Lys Leu
 1               5                  10                  15

Asp Arg Ile Arg Glu Ala Ser Gly Leu Gly Cys Lys Val Leu Arg Arg
                20                  25                  30

Arg

<210> SEQ ID NO 143
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 143

Pro Leu Ser Lys Gly Cys Phe Gly Leu Lys Leu Asp Arg Ile Arg Glu
 1               5                  10                  15

Ala Ser Gly Leu Gly Cys Lys Val Leu Arg Arg His
                20                  25

<210> SEQ ID NO 144
<211> LENGTH: 28
<212> TYPE: PRT
<213> ORGANISM: Artificial Sequence
<220> FEATURE:

-continued

<223> OTHER INFORMATION: synthetically generated polypeptide

<400> SEQUENCE: 144

Gly Ile Ser Lys Gly Cys Phe Gly Leu Lys Leu Asp Arg Ile Arg Glu
1               5                   10                  15

Ala Ser Gly Leu Gly Cys Lys Val Leu Arg Arg His
            20                  25

<210> SEQ ID NO 145
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 145

Gly Leu Thr Lys Gly Cys Phe Gly Leu Lys Leu Asp Arg Ile Arg Glu
1               5                   10                  15

Ala Ser Gly Leu Gly Cys Lys Val Leu Arg Arg His
            20                  25

<210> SEQ ID NO 146
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 146

Gly Leu Ser Arg Gly Cys Phe Gly Leu Lys Leu Asp Arg Ile Arg Glu
1               5                   10                  15

Ala Ser Gly Leu Gly Cys Lys Val Leu Arg Arg His
            20                  25

<210> SEQ ID NO 147
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 147

Gly Leu Ser Lys Gly Cys Phe Gly Leu Lys Leu Asp Arg Ile Arg Glu
1               5                   10                  15

Ala Ser Gly Leu Gly Cys Lys Val Ile Arg Arg His
            20                  25

<210> SEQ ID NO 148
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 148

Gly Leu Ser Lys Gly Cys Phe Gly Leu Lys Leu Asp Arg Ile Arg Glu
1               5                   10                  15

Ala Ser Gly Leu Gly Cys Lys Val Leu Lys Arg His
            20                  25

<210> SEQ ID NO 149
<211> LENGTH: 28
<212> TYPE: PRT
<213> ORGANISM: Artificial Sequence
<220> FEATURE:

```
<223> OTHER INFORMATION: synthetically generated polypeptide

<400> SEQUENCE: 149

Gly Leu Ser Lys Gly Cys Phe Gly Leu Lys Leu Asp Arg Ile Arg Glu
 1               5                  10                  15

Ala Ser Gly Leu Gly Cys Lys Val Leu Arg Lys His
            20                  25

<210> SEQ ID NO 150
<211> LENGTH: 28
<212> TYPE: PRT
<213> ORGANISM: Artificial Sequence
<220> FEATURE:
<223> OTHER INFORMATION: synthetically generated polypeptide

<400> SEQUENCE: 150

Gly Leu Ser Lys Gly Cys Phe Gly Leu Lys Leu Asp Arg Ile Arg Glu
 1               5                  10                  15

Ala Ser Gly Leu Gly Cys Lys Val Leu Arg Arg Arg
            20                  25
```

NATRIURETIC POLYPEPTIDES FOR REDUCING OR PREVENTING RESTENOSIS

CROSS-REFERENCE TO RELATED APPLICATIONS

This application is a National Stage application under 35 U.S.C. 371 of International Application No. PCT/US2009/069687 having an International Filing Date of Dec. 29, 2009, which claims benefit of priority from U.S. Provisional Application Ser. No. 61/141,127, filed on Dec. 29, 2008.

TECHNICAL FIELD

This document relates to natriuretic polypeptides. For example, this document provides methods and materials related to natriuretic polypeptides and the use of natriuretic polypeptides to prevent restenosis.

BACKGROUND

Natriuretic polypeptides (NPs) are polypeptides that can cause natriuresis (increased sodium excretion in the urine). Such polypeptides can be produced by brain, heart, kidney, and/or vascular tissue. The natriuretic peptide family in humans includes the cardiac hormones atrial natriuretic peptide (ANP), B-type natriuretic peptide (BNP), C-type natriuretic peptide (CNP), and urodilatin (URO). Natriuretic polypeptides function via well-characterized guanylyl cyclase receptors (i.e., NPR-A for ANP, BNP, and URO; and NPR-B for CNP) and the second messenger cyclic 3'5' guanosine monophosphate (cGMP) (Kuhn (2003) *Circ Res* 93:700-709; Tawaragi et al. (1991) *Biochem. Biophys. Res. Commun.* 175:645-651; and Komatsu et al. (1991) *Endocrinol.* 129:1104-1106).

SUMMARY

This document is based in part on the discovery that both naturally occurring and synthetic natriuretic polypeptides can have antiproliferative actions on human aortic vascular smooth muscle cells (HAoSMC) in culture. Thus, natriuretic polypeptides may be useful to reduce or prevent restenosis, for example.

In one aspect, this document features a method for reducing restenosis in a subject identified as being in need thereof, comprising administering to the subject a composition comprising a restenosis-reducing amount of a composition comprising a pharmaceutically acceptable carrier and a natriuretic polypeptide. The natriuretic polypeptide can be a chimeric natriuretic polypeptide comprising (a) the ring structure of a first natriuretic polypeptide or a variant of the ring structure of the first natriuretic polypeptide, and (b) an amino acid sequence from a second natriuretic polypeptide or a variant of the amino acid sequence from the second natriuretic polypeptide. The natriuretic polypeptide can comprise the amino acid sequence set forth in SEQ ID NO:1, but with one, two, three, four, or five amino acid substitutions relative to the sequence set forth in SEQ ID NO:1, the amino acid sequence set forth in SEQ ID NO:2, but with one, two, three, four, or five amino acid substitutions relative to the sequence set forth in SEQ ID NO:2, the amino acid sequence set forth in SEQ ID NO:3, but with one, two, three, four, or five amino acid substitutions relative to the sequence set forth in SEQ ID NO:3, the amino acid sequence set forth in SEQ ID NO:9, or the amino acid sequence set forth in SEQ ID NO:9 with one, two, three, four, or five amino acid substitutions relative to the sequence set forth in SEQ ID NO:9, the amino acid sequence set forth in SEQ ID NO:13, or the amino acid sequence set forth in SEQ ID NO:13 with one, two, three, four, or five amino acid substitutions relative to the sequence set forth in SEQ ID NO:13, the amino acid sequence set forth in SEQ ID NO:27, or the amino acid sequence set forth in SEQ ID NO:27 with one, two, three, four, or five amino acid substitutions relative to the sequence set forth in SEQ ID NO:27, the amino acid sequence set forth in SEQ ID NO:29, or the amino acid sequence set forth in SEQ ID NO:29 with one, two, three, four, or five amino acid substitutions relative to the sequence set forth in SEQ ID NO:29, or the amino acid sequence set forth in SEQ ID NO:30, or the amino acid sequence set forth in SEQ ID NO:30 with one, two, three, four, or five amino acid substitutions relative to the sequence set forth in SEQ ID NO:30.

The method can include administering the composition as a continuous intravenous infusion (e.g., for about one to about seven days). The method can include administering the composition as a continuous intravenous infusion for about one to about seven days, and subsequently administering the composition subcutaneously for about five to about 30 days. The method can include administering the composition as a continuous intravenous infusion at a dose of about 0.1 ng polypeptide/kg body mass/minute to about 30 ng polypeptide/kg body mass/minute, and subsequently administering the composition subcutaneously at a dose of about 10 ng polypeptide/kg body mass/day to about 30 ng polypeptide/kg body mass/day. The method can include administering the composition as a continuous intravenous infusion at a dose of about 0.1 ng polypeptide/kg body mass/minute to about 30 ng polypeptide/kg body mass/minute for about three hours to about seven days, and subsequently administering the composition subcutaneously at a dose of about 10 ng polypeptide/kg body mass/day to about 30 ng polypeptide/kg body mass/day for about five to about 30 days. The subject can be an angioplasty or stent placement patient. The method can include administering the continuous intravenous infusion beginning at or about the time of reperfusion. The composition can be administered beginning about three hours after the onset of reperfusion. The composition can be administered from about three hours to about 12 hours after reperfusion. The method can include administering the composition at a dose of about 1 ng polypeptide/kg body mass/minute to about 30 ng polypeptide/kg body mass/minute. The composition can be on an implanted medical device (e.g., a stent).

In another aspect, this document features a method for reducing proliferation of smooth muscle cells, comprising contacting the smooth muscle cells with an effective amount of a composition comprising a pharmaceutically acceptable carrier and a natriuretic polypeptide. The natriuretic polypeptide can be a chimeric natriuretic polypeptide comprising (a) the ring structure of a first natriuretic polypeptide or a variant of the ring structure of the first natriuretic polypeptide, and (b) an amino acid sequence from a second natriuretic polypeptide or a variant of the amino acid sequence from said second natriuretic polypeptide. The natriuretic polypeptide can comprise the amino acid sequence set forth in SEQ ID NO:1, but with one, two, three, four, or five amino acid substitutions relative to the sequence set forth in SEQ ID NO:1, the amino acid sequence set forth in SEQ ID NO:2, but with one, two, three, four, or five amino acid substitutions relative to the sequence set forth in SEQ ID NO:2, the amino acid sequence set forth in SEQ ID NO:3, but with one, two, three, four, or five amino acid substitutions relative to the sequence set forth in SEQ ID NO:3, the amino acid sequence set forth in SEQ ID NO:9, or the amino acid sequence set forth in SEQ ID NO:9 with one, two, three, four, or five amino acid substitutions relative to the sequence set forth in SEQ ID NO:9, the amino acid sequence set forth in SEQ ID NO:13, or the amino acid sequence set forth in SEQ ID NO:13 with one, two, three, four, or five amino acid substitutions relative to the sequence set forth in SEQ ID NO:13, the amino acid sequence set forth in SEQ ID NO:27, or the amino acid sequence set forth in SEQ ID NO:27 with one, two, three, four, or five amino acid substitutions relative to the sequence set forth in SEQ ID NO:27, the amino acid sequence set forth in SEQ ID NO:29, or the amino acid sequence set forth in SEQ ID NO:29 with one, two, three, four, or five amino acid substitutions relative to the sequence set forth in SEQ ID NO:29, or the amino acid sequence set forth in SEQ ID NO:30, or the amino acid sequence set forth in SEQ ID NO:30 with one, two, three, four, or five amino acid substitutions relative to the sequence set forth in SEQ ID NO:30.

This document also features the use of a natriuretic polypeptide and a pharmaceutically acceptable carrier in the manufacture of a medicament for reducing restenosis. The natriuretic polypeptide can be a chimeric natriuretic polypeptide comprising (a) the ring structure of a first natriuretic polypeptide or a variant of the ring structure of said first natriuretic polypeptide, and (b) an amino acid sequence from a second natriuretic polypeptide or a variant of said amino acid sequence from said second natriuretic polypeptide. The natriuretic polypeptide can comprise the amino acid sequence set forth in SEQ ID NO:1, but with one, two, three, four, or five amino acid substitutions relative to the sequence set forth in SEQ ID NO:1, the amino acid sequence set forth in SEQ ID NO:2, but with one, two, three, four, or five amino acid substitutions relative to the sequence set forth in SEQ ID NO:2, the amino acid sequence set forth in SEQ ID NO:3, but with one, two, three, four, or five amino acid substitutions relative to the sequence set forth in SEQ ID NO:3, the amino acid sequence set forth in SEQ ID NO:9, or the amino acid sequence set forth in SEQ ID NO:9 with one, two, three, four, or five amino acid substitutions relative to the sequence set forth in SEQ ID NO:9, the amino acid sequence set forth in SEQ ID NO:13, or the amino acid sequence set forth in SEQ ID NO:13 with one, two, three, four, or five amino acid substitutions relative to the sequence set forth in SEQ ID NO:13, the amino acid sequence set forth in SEQ ID NO:27, or the amino acid sequence set forth in SEQ ID NO:27 with one, two, three, four, or five amino acid substitutions relative to the sequence set forth in SEQ ID NO:27, the amino acid sequence set forth in SEQ ID NO:29, or the amino acid sequence set forth in SEQ ID NO:29 with one, two, three, four, or five amino acid substitutions relative to the sequence set forth in SEQ ID NO:29, or the amino acid sequence set forth in SEQ ID NO:30, or the amino acid sequence set forth in SEQ ID NO:30 with one, two, three, four, or five amino acid substitutions relative to the sequence set forth in SEQ ID NO:30.

The medicament can be formulated for intravenous infusion (e.g., continuous intravenous infusion for about one to about seven days). The medicament can be formulated for continuous intravenous infusion for about one to about seven days, and subsequent subcutaneous administration for about five to about 30 days (e.g., continuous intravenous infusion at a dose of about 0.1 ng polypeptide/kg body mass/minute to about 30 ng polypeptide/kg body mass/minute, and subsequent subcutaneous administration at a dose of about 10 ng polypeptide/kg body mass/day to about 30 ng polypeptide/kg body mass/day, or continuous intravenous infusion at a dose of about 0.1 ng polypeptide/kg body mass/minute to about 30 ng polypeptide/kg body mass/minute for about three hours to about seven days, and subsequent subcutaneous administration at a dose of about 10 ng polypeptide/kg body mass/day to about 30 ng polypeptide/kg body mass/day for about five to about 30 days). The medicament can be on an implantable medical device (e.g., a stent).

In yet another aspect, this document features the use of a natriuretic polypeptide and a pharmaceutically acceptable carrier in the manufacture of a medicament for reducing proliferation of smooth muscle cells. The natriuretic polypeptide can be a chimeric natriuretic polypeptide comprising (a) the ring structure of a first natriuretic polypeptide or a variant of the ring structure of said first natriuretic polypeptide, and (b) an amino acid sequence from a second natriuretic polypeptide or a variant of said amino acid sequence from said second natriuretic polypeptide. The natriuretic polypeptide can comprise the amino acid sequence set forth in SEQ ID NO:1, but with one, two, three, four, or five amino acid substitutions relative to the sequence set forth in SEQ ID NO:1, the amino acid sequence set forth in SEQ ID NO:2, but with one, two, three, four, or five amino acid substitutions relative to the sequence set forth in SEQ ID NO:2, the amino acid sequence set forth in SEQ ID NO:3, but with one, two, three, four, or five amino acid substitutions relative to the sequence set forth in SEQ ID NO:3, the amino acid sequence set forth in SEQ ID NO:9, or the amino acid sequence set forth in SEQ ID NO:9 with one, two, three, four, or five amino acid substitutions relative to the sequence set forth in SEQ ID NO:9, the amino acid sequence set forth in SEQ ID NO:13, or the amino acid sequence set forth in SEQ ID NO:13 with one, two, three, four, or five amino acid substitutions relative to the sequence set forth in SEQ ID NO:13, the amino acid sequence set forth in SEQ ID NO:27, or the amino acid sequence set forth in SEQ ID NO:27 with one, two, three, four, or five amino acid substitutions relative to the sequence set forth in SEQ ID NO:27, the amino acid sequence set forth in SEQ ID NO:29, or the amino acid sequence set forth in SEQ ID NO:29 with one, two, three, four, or five amino acid substitutions relative to the sequence set forth in SEQ ID NO:29, or the amino acid sequence set forth in SEQ ID NO:30, or the amino acid sequence set forth in SEQ ID NO:30 with one, two, three, four, or five amino acid substitutions relative to the sequence set forth in SEQ ID NO:30.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Natriuretic Compounds

Figure 1:
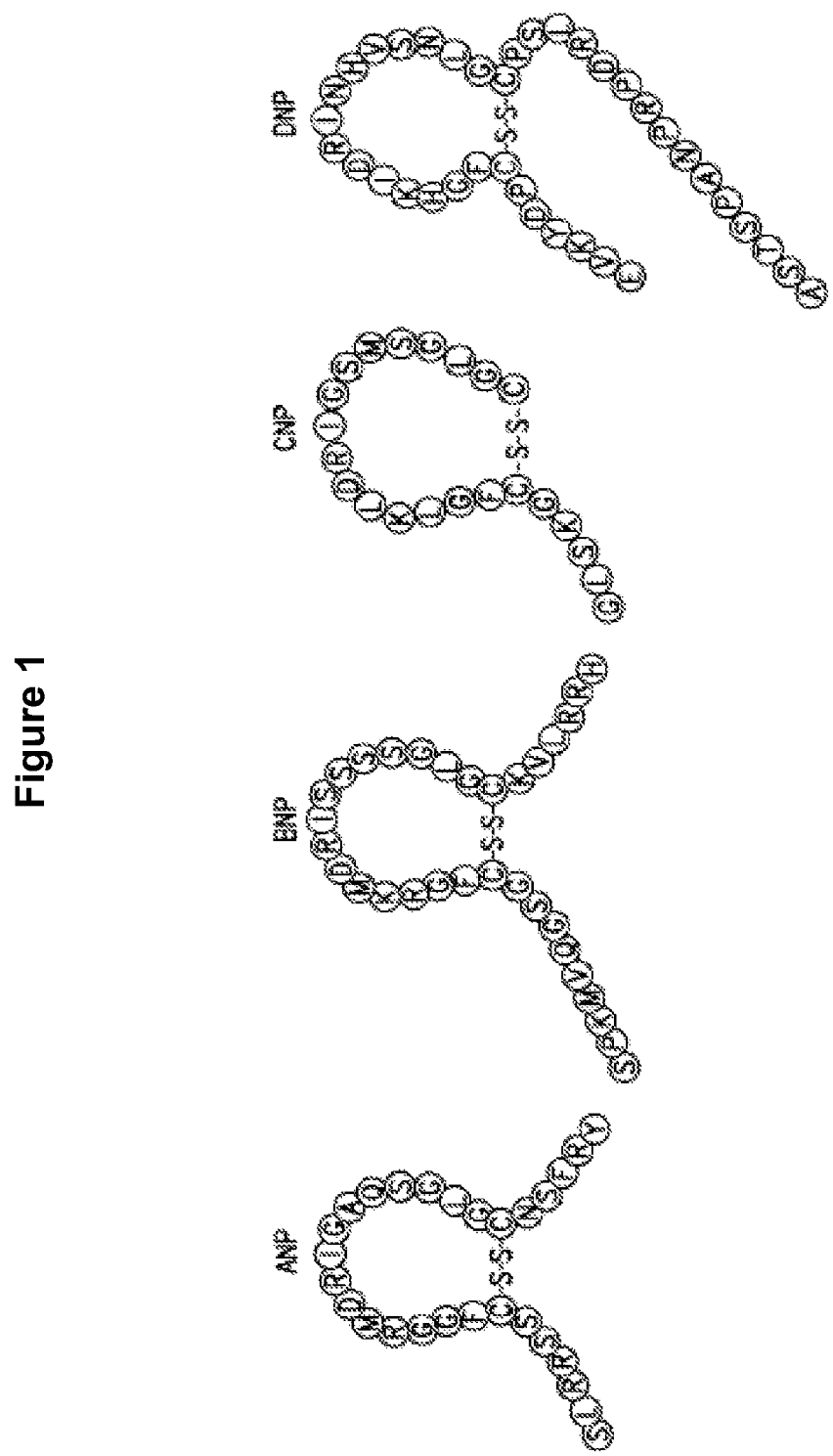
FIG. 1 is a drawing showing the amino acid sequences and structures of ANP (SEQ ID NO:1), BNP (SEQ ID NO:2), CNP (SEQ ID NO:3), and DNP (SEQ ID NO:5).

This document provides natriuretic compounds (e.g., polypeptides) and compositions that can be used to increase natriuretic activity in a subject in need thereof. For example, isolated NPs can increase plasma cGMP levels, urinary cGMP excretion, net renal cGMP generation, urine flow, urinary sodium excretion, urinary potassium excretion, hematocrit, plasma BNP immunoreactivity, renal blood flow, and/or plasma ANP immunoreactivity, and decrease renal vascular resistance, proximal and distal fractional reabsorption of sodium, mean arterial pressure, pulmonary capillary wedge pressure, right atrial pressure, pulmonary arterial pressure, plasma renin activity, plasma angiotensin II levels, plasma aldosterone levels, renal perfusion pressure, and/or systemic vascular resistance. As described herein, NPs also may be useful to reduce or prevent restenosis that can occur, for example, after vascular surgery, cardiac surgery, interventional radiology, or interventional cardiology following angioplasty or stent placement. For example, ANP, BNP, CNP, and the designer natriuretic polypeptides CD-NP, CU-NP, ABC-NP, ABC-NP1, and BC-NP2 described herein can reduce proliferation of HAoSMC, as described in the Example below.

As used herein, the term "natriuretic polypeptide" or "NP" includes native (naturally occurring, wild type) NPs (e.g., ANP, BNP, CNP, and URO, as well as Dendroaspis natriuretic peptide (DNP)), one or more portions of a native NP, variants of a native NP, or chimeras of native NPs, portions of native NPs, or variants of native NPs or portions of native NPs. In some embodiments, a NP includes only portions of the mature form of a native NP. Chimeric NPs containing amino acid sequences from human CNP, BNP, and ANP or URO, or Dendroaspis DNP, can be particularly useful, although other NPs are contemplated herein.

The term "isolated polypeptide" refers to a polypeptide that (1) is not associated with proteins found in nature, (2) is free of other proteins from the same source (e.g., free of human proteins), (3) is expressed by a cell from a different species, or (4) does not occur in nature. An isolated polypeptide can be, for example, encoded by DNA or RNA, including synthetic DNA or RNA, or some combination thereof.

Amino acid sequences for endogenous human mature NPs include the following:

```
ANP:
                                   (SEQ ID NO: 1)
SLRRSSCFGGRMDRIGAQSGLGCNSFRY

BNP:
                                   (SEQ ID NO: 2)
SPKMVQGSGCFGRKMDRISSSSGLGCKVLRRH

CNP:
                                   (SEQ ID NO: 3)
GLSKGCFGLKLDRIGSMSGLGC

URO:
                                   (SEQ ID NO: 4)
TAPRSLRRSSCFGGRMDRIGAQSGLGCNSFRY
```

In addition, the native Dendroaspis amino acid sequence for DNP is

```
                                   (SEQ ID NO: 5)
EVKYDPCFGHKIDRINHVSNLGCPSLRDPRPNAPSTSA
```

Chimeric NPs can include amino acid sequences from two or more individual NPs. In some embodiments, for example, a chimeric polypeptide can include amino acid sequences from ANP and CNP; BNP and CNP; ANP, BNP, and CNP; CNP and URO; CNP and DNP; or CNP, URO, and BNP. In some cases, a chimeric NP can include a ring structure and cysteine bond (e.g., the ring structure and cysteine bond of ANP, BNP, CNP, or DNP) in combination with one or more amino acid segments from another NP. The chimeric NPs described herein are non-limiting examples of polypeptides that can be useful to prevent or reduce restenosis, for example.

In some embodiments, a chimeric BD-NP can include the N-terminal 26 amino acids of human BNP (SPKMVQGS-GCFGRKMDRISSSSGLGC; SEQ ID NO:6) and the C-terminal 15 amino acids of DNP (PSLRDPRPNAPSTSA; SEQ ID NO:7), and can have the amino acid sequence SPKM-VQGSGCFGRKMDRISSSSGLGCPSLRDPRPNAPSTSA (SEQ ID NO:8).

In some embodiments, a chimeric CD-NP can include the amino acid sequence of human CNP (GLSKGCFGLKLD-RIGSMSGLGC; SEQ ID NO:3) and the C-terminal 15 amino acids of DNP (PSLRDPRPNAPSTSA; SEQ ID NO:7), and can have the amino acid sequence GLSKGCFGLKLD-RIGSMSGLGCPSLRDPRPNAPSTSA (SEQ ID NO:9).

In some embodiments, a chimeric CU-NP can include the N-terminal ten amino acids of human URO (TAPRSLRRSS; SEQ ID NO:10), the 17 amino acid ring structure and disulfide bond of human CNP (CFGLKLDRIGSMSGLGC; SEQ ID NO:11), and the C-terminal five amino acids of human URO (NSFRY; SEQ ID NO:12), and can have the amino acid sequence TAPRSLRRSSCFGLKLDRIGSMS-GLGCNSFRY (SEQ ID NO:13).

In some embodiments, a chimeric BAA-NP can include the N-terminal six amino acids of human ANP (SLRRSS; SEQ ID NO:14), the 17 amino acid ring structure and disulfide bond of human BNP (CFGRKMDRISSSSGLGC; SEQ ID NO:15), and the C-terminal five amino acids of human ANP (NSFRY; SEQ ID NO:12), and can have the amino acid sequence SLRRSSCFGRKMDRISSSSGLGCNSFRY (SEQ ID NO:16).

In some embodiments, a chimeric BUA-NP can include the N-terminal 10 amino acids of human URO (TAPRSLRRSS; SEQ ID NO:10), the 17 amino acid ring structure and disulfide bond of human BNP (CFGRKMDRISSSSGLGC; SEQ ID NO:15), and the C-terminal 5 amino acids of human ANP (NSFRY; SEQ ID NO:12), and can have the amino acid sequence TAPRSLRRSSCFGRKMDRISSSSGLGCNSFRY (SEQ ID NO:17).

In some embodiments, a chimeric CAA-NP can include the N-terminal 6 amino acids of human ANP (SLRRSS; SEQ ID NO:14), the 17 amino acid ring structure and disulfide bond of human CNP (CFGLKLDRIGSMSGLGC; SEQ ID NO:11), and the C-terminal 5 amino acids of human ANP (NSFRY; SEQ ID NO:12), and can have the amino acid sequence SLRRSSCFGLKLDRIGSMSGLGCNSFRY (SEQ ID NO:18).

As another example, in some embodiments, a chimeric CAB-NP can include the N-terminal six amino acids of human ANP (SLRRSS; SEQ ID NO:14), the 17 amino acid ring structure and disulfide bond of human CNP (CFGLKLD-RIGSMSGLGC; SEQ ID NO:11), and the C-terminal six amino acids of human BNP (KVLRRH; SEQ ID NO:19), and can have the amino acid sequence SLRRSSCFGLKLD-RIGSMSGLGCKVLRRH (SEQ ID NO:20).

In some embodiments, a chimeric CBB-NP can include the N-terminal nine amino acids of human BNP (SPKMVQGSG; SEQ ID NO:21), the 17 amino acid ring structure and disulfide bond of human CNP (CFGLKLDRIGSMSGLGC; SEQ ID NO:11), and the C-terminal six amino acids of human BNP (KVLRRH; SEQ ID NO:19), and can have the amino acid sequence SPKMVQGSGCFGLKLDRIGSMSGLGCKVLRRH (SEQ ID NO:22).

In some embodiments, a chimeric CDD-NP can include the N-terminal six amino acids of DNP (EVKYDP; SEQ ID NO:23), the 17 amino acid ring structure and disulfide bond of human CNP (CFGLKLDRIGSMSGLGC; SEQ ID NO:11), and the C-terminal 15 amino acids of DNP (PSLRDPRPNAPSTSA; SEQ ID NO:7), and can have the amino acid sequence EVKYDPCFGLKLDRIGSMSGLGCPSLRDPRPNAPSTSA (SEQ ID NO:24).

In some embodiments, a chimeric CUB-NP can include the N-terminal 10 amino acids of human URO (TAPRSLRRSS; SEQ ID NO:10), the 17 amino acid ring structure and disulfide bond of human CNP (CFGLKLDRIGSMSGLGC; SEQ ID NO:11), and the C-terminal six amino acids of human BNP (KVLRRH; SEQ ID NO:19), and can have the amino acid sequence TAPRSLRRSSCFGLKLDRIGSMSGLGCKVLRRH (SEQ ID NO:25).

In some embodiments, a chimeric ABC-NP1 can include amino acids 11 to 15 of human ANP (RMDR1; SEQ ID NO:26) at its amino terminus, followed by the amino acid sequence of human CNP (GLSKGCFGLKLDRIGSMSGLGC; SEQ ID NO:3), and the C-terminal six amino acids of human BNP (KVLRRH; SEQ ID NO:19), and can have the amino acid sequence RMDRIGLSKGCFGLKLDRIGSMSGLGCKVLRRH (SEQ ID NO:27).

In some cases, a chimeric NP can include a variant (e.g., a substitution, addition, or deletion) at one or more positions (e.g., one, two, three, four, five, six, seven, eight, nine, or ten positions) with respect to any of SEQ ID NOS:1 to 27. For example, a chimeric ABC-NP can include amino acids 11 to 15 of human ANP (RMDR1; SEQ ID NO:26) at its amino terminus, followed by the amino acid sequence of human CNP with the exception that the amino acid residues at positions 15, 16, and 17 are changed to Arg, Glu, and Ala (GLSKGCFGLKLDRIREASGLGC; SEQ ID NO:28), and the C-terminal six amino acids of human BNP (KVLRRH; SEQ ID NO:19), and can have the amino acid RMDRIGLSKGCFGLKLDRIREASGLGCKVLRRH (SEQ ID NO:29). A chimeric BC-NP2 can include the amino acid sequence of human CNP with the exception that the amino acid residues at positions 15, 16, and 17 are changed to Arg, Glu, and Ala (GLSKGCFGLKLDRIREASGLGC; SEQ ID NO:28), followed by the C-terminal six amino acids of human BNP (KVLRRH; SEQ ID NO:19), and can have the amino acid sequence GLSKGCFGLKLDRIREASGLGCKVLRRH (SEQ ID NO:30).

Variant NPs, e.g., those having one or more amino acid substitutions relative to a native NP amino acid sequence, can be prepared and modified as described herein. Amino acid substitutions can be made, in some cases, by selecting substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine) Substitutions made within these groups can be considered conservative substitutions. Non-limiting examples of useful substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine.

Non-limiting examples of variant chimeric NPs include the following:

```
                                        (SEQ ID NO: 31)
TLRRSSCFGGRMDRIGAQSGLGCNSFRY (SEQ ID NO: 32)
SIRRSSCFGGRMDRIGAQSGLGCNSFRY (SEQ ID NO: 33)
SLKRSSCFGGRMDRIGAQSGLGCNSFRY (SEQ ID NO: 34)
SLRKSSCFGGRMDRIGAQSGLGCNSFRY (SEQ ID NO: 35)
SLRRSSCFGGRMDRIGAQSGLGCNTFRY (SEQ ID NO: 36)
SLRRSSCFGGRMDRIGAQSGLGCNSLRY (SEQ ID NO: 37)
SLRRSSCFGGRMDRIGAQSGLGCNSFKY (SEQ ID NO: 38)
SLRRSSCFGGRMDRIGAQSGLGCNSFRF (SEQ ID NO: 39)
TPKMVQGSGCFGRKMDRISSSSGLGCKVLRRH (SEQ ID NO: 40)
SGKMVQGSGCFGRKMDRISSSSGLGCKVLRRH (SEQ ID NO: 41)
SPRMVQGSGCFGRKMDRISSSSGLGCKVLRRH (SEQ ID NO: 42)
SPKLVQGSGCFGRKMDRISSSSGLGCKVLRRH (SEQ ID NO: 43)
SPKMVQGSGCFGRKMDRISSSSGLGCKVIRRH (SEQ ID NO: 44)
SPKMVQGSGCFGRKMDRISSSSGLGCKVLKRH (SEQ ID NO: 45)
SPKMVQGSGCFGRKMDRISSSSGLGCKVLRKH (SEQ ID NO: 46)
SPKMVQGSGCFGRKMDRISSSSGLGCKVLRRR (SEQ ID NO: 47)
PLSKGCFGLKLDRIGSMSGLGC (SEQ ID NO: 48)
GISKGCFGLKLDRIGSMSGLGC (SEQ ID NO: 49)
GLTKGCFGLKLDRIGSMSGLGC
```

```
                                                   (SEQ ID NO: 50)
GLSRGCFGLKLDRIGSMSGLGC (SEQ ID NO: 51)
GLSKGCFGLKLDRIGSMSPLGC (SEQ ID NO: 52)
GLSKGCFGLKLDRIGSMSGIGC (SEQ ID NO: 53)
GLSKGCFGLKLDRIGSMSGLPC (SEQ ID NO: 54)
GLSKGCFGLKLDRIGSMSGLGS (SEQ ID NO: 55)
TPKMVQGSGCFGRKMDRISSSSGLGCPSLRDPRPNAPSTSA (SEQ ID NO: 56)
SGKMVQGSGCFGRKMDRISSSSGLGCPSLRDPRPNAPSTSA (SEQ ID NO: 57)
SPRMVQGSGCFGRKMDRISSSSGLGCPSLRDPRPNAPSTSA (SEQ ID NO: 58)
SPKLVQGSGCFGRKMDRISSSSGLGCPSLRDPRPNAPSTSA (SEQ ID NO: 59)
SPKMVQGSGCFGRKMDRISSSSGLGCPSLRDPRPNAPTTSA (SEQ ID NO: 60)
SPKMVQGSGCFGRKMDRISSSSGLGCPSLRDPRPNAPSSSA (SEQ ID NO: 61)
SPKMVQGSGCFGRKMDRISSSSGLGCPSLRDPRPNAPSTTA (SEQ ID NO: 62)
SPKMVQGSGCFGRKMDRISSSSGLGCPSLRDPRPNAPSTSV (SEQ ID NO: 63)
PLSKGCFGLKLDRIGSMSGLGCPSLRDPRPNAPSTSA (SEQ ID NO: 64)
GISKGCFGLKLDRIGSMSGLGCPSLRDPRPNAPSTSA (SEQ ID NO: 65)
GLTKGCFGLKLDRIGSMSGLGCPSLRDPRPNAPSTSA (SEQ ID NO: 66)
GLSRGCFGLKLDRIGSMSGLGCPSLRDPRPNAPSTSA (SEQ ID NO: 67)
GLSKGCFGLKLDRIGSMSGLGCPSLRDPRPNAPTTSA (SEQ ID NO: 68)
GLSKGCFGLKLDRIGSMSGLGCPSLRDPRPNAPSSSA (SEQ ID NO: 69)
GLSKGCFGLKLDRIGSMSGLGCPSLRDPRPNAPSTTA (SEQ ID NO: 70)
GLSKGCFGLKLDRIGSMSGLGCPSLRDPRPNAPSTSV (SEQ ID NO: 71)
SAPRSLRRSSCFGLKLDRIGSMSGLGCNSFRY (SEQ ID NO: 72)
TVPRSLRRSSCFGLKLDRIGSMSGLGCNSFRY (SEQ ID NO: 73)
TAGRSLRRSSCFGLKLDRIGSMSGLGCNSFRY (SEQ ID NO: 74)
TAPKSLRRSSCFGLKLDRIGSMSGLGCNSFRY (SEQ ID NO: 75)
TAPRSLRRSSCFGLKLDRIGSMSGLGCNTFRY (SEQ ID NO: 76)
TAPRSLRRSSCFGLKLDRIGSMSGLGCNSLRY (SEQ ID NO: 77)
TAPRSLRRSSCFGLKLDRIGSMSGLGCNSFKY (SEQ ID NO: 78)
TAPRSLRRSSCFGLKLDRIGSMSGLGCNSFRF (SEQ ID NO: 79)
TLRRSSCFGRKMDRISSSSGLGCNSFRY (SEQ ID NO: 80)
SIRRSSCFGRKMDRISSSSGLGCNSFRY (SEQ ID NO: 81)
SLKRSSCFGRKMDRISSSSGLGCNSFRY (SEQ ID NO: 82)
SLRKSSCFGRKMDRISSSSGLGCNSFRY (SEQ ID NO: 83)
SLRRSSCFGRKMDRISSSSGLGCNTFRY (SEQ ID NO: 84)
SLRRSSCFGRKMDRISSSSGLGCNSLRY (SEQ ID NO: 85)
SLRRSSCFGRKMDRISSSSGLGCNSFKY (SEQ ID NO: 86)
SLRRSSCFGRKMDRISSSSGLGCNSFRF (SEQ ID NO: 87)
SAPRSLRRSSCFGRKMDRISSSSGLGCNSFRY (SEQ ID NO: 88)
TVPRSLRRSSCFGRKMDRISSSSGLGCNSFRY (SEQ ID NO: 89)
TAGRSLRRSSCFGRKMDRISSSSGLGCNSFRY (SEQ ID NO: 90)
TAPKSLRRSSCFGRKMDRISSSSGLGCNSFRY (SEQ ID NO: 91)
TAPRSLRRSSCFGRKMDRISSSSGLGCNTFRY (SEQ ID NO: 92)
TAPRSLRRSSCFGRKMDRISSSSGLGCNSLRY (SEQ ID NO: 93)
TAPRSLRRSSCFGRKMDRISSSSGLGCNSFKY (SEQ ID NO: 94)
TAPRSLRRSSCFGRKMDRISSSSGLGCNSFRF (SEQ ID NO: 95)
TLRRSSCFGLKLDRIGSMSGLGCKVLRRH (SEQ ID NO: 96)
SIRRSSCFGLKLDRIGSMSGLGCKVLRRH (SEQ ID NO: 97)
SLKRSSCFGLKLDRIGSMSGLGCKVLRRH (SEQ ID NO: 98)
SLRKSSCFGLKLDRIGSMSGLGCKVLRRH (SEQ ID NO: 99)
SLRRSSCFGLKLDRIGSMSGLGCKVIRRH (SEQ ID NO: 100)
SLRRSSCFGLKLDRIGSMSGLGCKVLKRH (SEQ ID NO: 101)
SLRRSSCFGLKLDRIGSMSGLGCKVLRKH (SEQ ID NO: 102)
SLRRSSCFGLKLDRIGSMSGLGCKVLRRR (SEQ ID NO: 103)
TPKMVQGSGCFGLKLDRIGSMSGLGCKVLRRH
```

```
                                        (SEQ ID NO: 104)
SGKMVQGSGCFGLKLDRIGSMSGLGCKVLRRH (SEQ ID NO: 105)
SPRMVQGSGCFGLKLDRIGSMSGLGCKVLRRH (SEQ ID NO: 106)
SPKLVQGSGCFGLKLDRIGSMSGLGCKVLRRH (SEQ ID NO: 107)
SPKMVQGSGCFGLKLDRIGSMSGLGCKVIRRH (SEQ ID NO: 108)
SPKMVQGSGCFGLKLDRIGSMSGLGCKVLRRH (SEQ ID NO: 109)
SPKMVQGSGCFGLKLDRIGSMSGLGCKVLRKH (SEQ ID NO: 110)
SPKMVQGSGCFGLKLDRIGSMSGLGCKVLRRR (SEQ ID NO: 111)
DVKYDPCFGLKLDRIGSMSGLGCPSLRDPRPNAPSTSA (SEQ ID NO: 112)
ELKYDPCFGLKLDRIGSMSGLGCPSLRDPRPNAPSTSA (SEQ ID NO: 113)
EVRYDPCFGLKLDRIGSMSGLGCPSLRDPRPNAPSTSA (SEQ ID NO: 114)
EVKFDPCFGLKLDRIGSMSGLGCPSLRDPRPNAPSTSA (SEQ ID NO: 115)
EVKYDPCFGLKLDRIGSMSGLGCPSLRDPRPNAPTTSA (SEQ ID NO: 116)
EVKYDPCFGLKLDRIGSMSGLGCPSLRDPRPNAPSSSA (SEQ ID NO: 117)
EVKYDPCFGLKLDRIGSMSGLGCPSLRDPRPNAPSTTA (SEQ ID NO: 118)
EVKYDPCFGLKLDRIGSMSGLGCPSLRDPRPNAPSTSV (SEQ ID NO: 119)
SAPRSLRRSSCFGLKLDRIGSMSGLGCKVLRRH (SEQ ID NO: 120)
TVPRSLRRSSCFGLKLDRIGSMSGLGCKVLRRH (SEQ ID NO: 121)
TAGRSLRRSSCFGLKLDRIGSMSGLGCKVLRRH (SEQ ID NO: 122)
TAPKSLRRSSCFGLKLDRIGSMSGLGCKVLRRH (SEQ ID NO: 123)
TAPRSLRRSSCFGLKLDRIGSMSGLGCKVIRRH (SEQ ID NO: 124)
TAPRSLRRSSCFGLKLDRIGSMSGLGCKVLKRH (SEQ ID NO: 125)
TAPRSLRRSSCFGLKLDRIGSMSGLGCKVLRKH (SEQ ID NO: 126)
TAPRSLRRSSCFGLKLDRIGSMSGLGCKVLRRR (SEQ ID NO: 127)
KMDRIGLSKGCFGLKLDRIGSMSGLGCKVLRRH (SEQ ID NO: 128)
RLDRIGLSKGCFGLKLDRIGSMSGLGCKVLRRH (SEQ ID NO: 129)
RMERIGLSKGCFGLKLDRIGSMSGLGCKVLRRH (SEQ ID NO: 130)
RMDKIGLSKGCFGLKLDRIGSMSGLGCKVLRRH (SEQ ID NO: 131)
RMDRIGLSKGCFGLKLDRIGSMSGLGCKVIRRH (SEQ ID NO: 132)
RMDRIGLSKGCFGLKLDRIGSMSGLGCKVLKRH (SEQ ID NO: 133)
RMDRIGLSKGCFGLKLDRIGSMSGLGCKVLRKH (SEQ ID NO: 134)
RMDRIGLSKGCFGLKLDRIGSMSGLGCKVLRRR (SEQ ID NO: 135)
KMDRIGLSKGCFGLKLDRIREASGLGCKVLRRH (SEQ ID NO: 136)
RLDRIGLSKGCFGLKLDRIREASGLGCKVLRRH (SEQ ID NO: 137)
RMERIGLSKGCFGLKLDRIREASGLGCKVLRRH (SEQ ID NO: 138)
RMDKIGLSKGCFGLKLDRIREASGLGCKVLRRH (SEQ ID NO: 139)
RMDRIGLSKGCFGLKLDRIREASGLGCKVIRRH (SEQ ID NO: 140)
RMDRIGLSKGCFGLKLDRIREASGLGCKVLKRH (SEQ ID NO: 141)
RMDRIGLSKGCFGLKLDRIREASGLGCKVLRKH (SEQ ID NO: 142)
RMDRIGLSKGCFGLKLDRIREASGLGCKVLRRR (SEQ ID NO: 143)
PLSKGCFGLKLDRIREASGLGCKVLRRH (SEQ ID NO: 144)
GISKGCFGLKLDRIREASGLGCKVLRRH (SEQ ID NO: 145)
GLTKGCFGLKLDRIREASGLGCKVLRRH (SEQ ID NO: 146)
GLSRGCFGLKLDRIREASGLGCKVLRRH (SEQ ID NO: 147)
GLSKGCFGLKLDRIREASGLGCKVIRRH (SEQ ID NO: 148)
GLSKGCFGLKLDRIREASGLGCKVLKRH (SEQ ID NO: 149)
GLSKGCFGLKLDRIREASGLGCKVLRKH (SEQ ID NO: 150)
GLSKGCFGLKLDRIREASGLGCKVLRRR
```

Further examples of conservative substitutions that can be made at any position within the polypeptides provided herein are set forth in Table 1.

TABLE 1

Examples of conservative amino acid substitutions

| Original Residue | Exemplary substitutions | Preferred substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |

TABLE 1-continued

Examples of conservative amino acid substitutions

| Original Residue | Exemplary substitutions | Preferred substitutions |
|---|---|---|
| Ile | Leu, Val, Met, Ala, Phe, Norleucine | Leu |
| Leu | Norleucine, Ile, Val, Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleucine | Leu |

In some embodiments, a NP can include one or more non-conservative substitutions. Non-conservative substitutions typically entail exchanging a member of one of the classes described above for a member of another class. Such production can be desirable to provide large quantities or alternative embodiments of such compounds. Whether an amino acid change results in a functional polypeptide can readily be determined by assaying the specific activity of the peptide variant.

A polypeptide provided herein can have any sequence and can have any length. For example, a polypeptide can include the sequences set forth in SEQ ID NOS:6 and 7. In some cases, a polypeptide provided herein can contain an amino acid sequence that aligns to (a) the sequence set forth in SEQ ID NO:6 with five or less (e.g., five or less, four or less, three or less, two or less, one, or zero) amino acid additions, deletions, substitutions, or combinations thereof, and (b) the sequence set forth in SEQ ID NO:7 with three or less (e.g., three or less, two or less, one, or zero) amino acid additions, deletions, substitutions, or combinations thereof. For example, a polypeptide provided herein can contain the sequence set forth in SEQ ID NO:8, with the exception that the first serine residue or the last alanine residue of SEQ ID NO:8 is deleted or replaced with a different amino acid residue.

In some cases, a polypeptide can include the sequences set forth in SEQ ID NOS:3 and 7. In some cases, a polypeptide provided herein can contain an amino acid sequence that aligns to (a) the sequence set forth in SEQ ID NO:3 with five or less (e.g., five or less, four or less, three or less, two or less, one, or zero) amino acid additions, deletions, substitutions, or combinations thereof, and (b) the sequence set forth in SEQ ID NO:7 with three or less (e.g., three or less, two or less, one, or zero) amino acid additions, deletions, substitutions, or combinations thereof. For example, a polypeptide provided herein can contain the sequence set forth in SEQ ID NO:9, with the exception that the first glycine residue or the last alanine residue of SEQ ID NO:9 is deleted or replaced with a different amino acid residue.

In some cases, a polypeptide can include the sequences set forth in SEQ ID NOS:10, 11, and 12. In some cases, a polypeptide provided herein can contain an amino acid sequence that aligns to (a) the sequence set forth in SEQ ID NO:10 with three or less (e.g., three or less, two or less, one, or zero) amino acid additions, deletions, substitutions, or combinations thereof, (b) the sequence set forth in SEQ ID NO:11 with five or less (e.g., five or less, four or less, three or less, two or less, one, or zero) amino acid additions, deletions, substitutions, or combinations thereof, and (c) the sequence set forth in SEQ ID NO:12 with two or less (e.g., two or less, one, or zero) amino acid additions, deletions, substitutions, or combinations thereof. For example, a polypeptide provided herein can contain the sequence set forth in SEQ ID NO:13, with the exception that the first threonine residue or the last tyrosine residue of SEQ ID NO:13 is deleted or replaced with a different amino acid residue.

In some cases, a polypeptide can include the sequences set forth in SEQ ID NOS:14, 15, and 12. In some cases, a polypeptide provided herein can contain an amino acid sequence that aligns to (a) the sequence set forth in SEQ ID NO:14 with two or less (e.g., two or less, one, or zero) amino acid additions, deletions, substitutions, or combinations thereof, (b) the sequence set forth in SEQ ID NO:15 with five or less (e.g., five or less, four or less, three or less, two or less, one, or zero) amino acid additions, deletions, substitutions, or combinations thereof, and (c) the sequence set forth in SEQ ID NO:12 with two or less (e.g., two or less, one, or zero) amino acid additions, deletions, substitutions, or combinations thereof. For example, a polypeptide provided herein can contain the sequence set forth in SEQ ID NO:16, with the exception that the first serine residue or the last tyrosine residue of SEQ ID NO:16 is deleted or replaced with a different amino acid residue.

In some cases, a polypeptide can include the sequences set forth in SEQ ID NOS:10, 15, and 12. In some cases, a polypeptide provided herein can contain an amino acid sequence that aligns to (a) the sequence set forth in SEQ ID NO:10 with three or less (e.g., three or less, two or less, one, or zero) amino acid additions, deletions, substitutions, or combinations thereof, (b) the sequence set forth in SEQ ID NO:15 with five or less (e.g., five or less, four or less, three or less, two or less, one, or zero) amino acid additions, deletions, substitutions, or combinations thereof, and (c) the sequence set forth in SEQ ID NO:12 with two or less (e.g., two or less, one, or zero) amino acid additions, deletions, substitutions, or combinations thereof. For example, a polypeptide provided herein can contain the sequence set forth in SEQ ID NO:17, with the exception that the first threonine residue or the last tyrosine residue of SEQ ID NO:17 is deleted or replaced with a different amino acid residue.

In some cases, a polypeptide can include the sequences set forth in SEQ ID NOS:14, 11, and 12. In some cases, a polypeptide provided herein can contain an amino acid sequence that aligns to (a) the sequence set forth in SEQ ID NO:14 with two or less (e.g., two or less, one, or zero) amino acid additions, deletions, substitutions, or combinations thereof, (b) the sequence set forth in SEQ ID NO:11 with five or less (e.g., five or less, four or less, three or less, two or less, one, or zero) amino acid additions, deletions, substitutions, or combinations thereof, and (c) the sequence set forth in SEQ ID NO:12 with two or less (e.g., two or less, one, or zero) amino acid additions, deletions, substitutions, or combinations thereof. For example, a polypeptide provided herein can contain the sequence set forth in SEQ ID NO:18, with the exception that the first serine residue or the last tyrosine residue of SEQ ID NO:18 is deleted or replaced with a different amino acid residue.

In some cases, a polypeptide can include the sequences set forth in SEQ ID NOS:14, 11, and 19. In some cases, a polypeptide provided herein can contain an amino acid sequence that aligns to (a) the sequence set forth in SEQ ID NO:14 with two or less (e.g., two or less, one, or zero) amino acid additions, deletions, substitutions, or combinations thereof, (b) the sequence set forth in SEQ ID NO:11 with five or less (e.g., five or less, four or less, three or less, two or less, one, or zero) amino acid additions, deletions, substitutions, or combinations thereof, and (c) the sequence set forth in SEQ ID NO:19 with two or less (e.g., two or less, one, or zero) amino acid additions, deletions, substitutions, or combinations thereof. For example, a polypeptide provided herein can contain the sequence set forth in SEQ ID NO:20, with the exception that the first serine residue or the last histidine residue of SEQ ID NO:20 is deleted or replaced with a different amino acid residue.

In some cases, a polypeptide can include the sequences set forth in SEQ ID NOS:21, 11, and 19. In some cases, a polypeptide provided herein can contain an amino acid sequence that aligns to (a) the sequence set forth in SEQ ID NO:21 with three or less (e.g., three or less, two or less, one, or zero) amino acid additions, deletions, substitutions, or combinations thereof, (b) the sequence set forth in SEQ ID NO:11 with five or less (e.g., five or less, four or less, three or less, two or less, one, or zero) amino acid additions, deletions, substitutions, or combinations thereof, and (c) the sequence set forth in SEQ ID NO:19 with two or less (e.g., two or less, one, or zero) amino acid additions, deletions, substitutions, or combinations thereof. For example, a polypeptide provided herein can contain the sequence set forth in SEQ ID NO:22, with the exception that the first serine residue or the last histidine residue of SEQ ID NO:22 is deleted or replaced with a different amino acid residue.

In some cases, a polypeptide can include the sequences set forth in SEQ ID NOS:23, 11, and 7. In some cases, a polypeptide provided herein can contain an amino acid sequence that aligns to (a) the sequence set forth in SEQ ID NO:23 with two or less (e.g., two or less, one, or zero) amino acid additions, deletions, substitutions, or combinations thereof, (b) the sequence set forth in SEQ ID NO:11 with five or less (e.g., five or less, four or less, three or less, two or less, one, or zero) amino acid additions, deletions, substitutions, or combinations thereof, and (c) the sequence set forth in SEQ ID NO:7 with five or less (e.g., five or less, four or less, three or less, two or less, one, or zero) amino acid additions, deletions, substitutions, or combinations thereof. For example, a polypeptide provided herein can contain the sequence set forth in SEQ ID NO:24, with the exception that the first glutamic acid residue or the last alanine residue of SEQ ID NO:24 is deleted or replaced with a different amino acid residue.

In some cases, a polypeptide can include the sequences set forth in SEQ ID NOS:10, 11, and 19. In some cases, a polypeptide provided herein can contain an amino acid sequence that aligns to (a) the sequence set forth in SEQ ID NO:10 with three or less (e.g., three or less, two or less, one, or zero) amino acid additions, deletions, substitutions, or combinations thereof, (b) the sequence set forth in SEQ ID NO:11 with five or less (e.g., five or less, four or less, three or less, two or less, one, or zero) amino acid additions, deletions, substitutions, or combinations thereof, and (c) the sequence set forth in SEQ ID NO:19 with two or less (e.g., two or less, one, or zero) amino acid additions, deletions, substitutions, or combinations thereof. For example, a polypeptide provided herein can contain the sequence set forth in SEQ ID NO:25, with the exception that the first threonine residue or the last histidine residue of SEQ ID NO:25 is deleted or replaced with a different amino acid residue.

In some cases, a polypeptide can include the sequences set forth in SEQ ID NOS:26, 3, and 19. In some cases, a polypeptide provided herein can contain an amino acid sequence that aligns to (a) the sequence set forth in SEQ ID NO:26 with two or less (e.g., two or less, one, or zero) amino acid additions, deletions, substitutions, or combinations thereof, (b) the sequence set forth in SEQ ID NO:3 with five or less (e.g., five or less, four or less, three or less, two or less, one, or zero) amino acid additions, deletions, substitutions, or combinations thereof, and (c) the sequence set forth in SEQ ID NO:19 with two or less (e.g., two or less, one, or zero) amino acid additions, deletions, substitutions, or combinations thereof. For example, a polypeptide provided herein can contain the sequence set forth in SEQ ID NO:27, with the exception that the first arginine residue or the last histidine residue of SEQ ID NO:27 is deleted or replaced with a different amino acid residue.

In some cases, a polypeptide can include the sequences set forth in SEQ ID NOS:26, 28, and 19. In some cases, a polypeptide provided herein can contain an amino acid sequence that aligns to (a) the sequence set forth in SEQ ID NO:26 with two or less (e.g., two or less, one, or zero) amino acid additions, deletions, substitutions, or combinations thereof, (b) the sequence set forth in SEQ ID NO:28 with five or less (e.g., five or less, four or less, three or less, two or less, one, or zero) amino acid additions, deletions, substitutions, or combinations thereof, and (c) the sequence set forth in SEQ ID NO:19 with two or less (e.g., two or less, one, or zero) amino acid additions, deletions, substitutions, or combinations thereof. For example, a polypeptide provided herein can contain the sequence set forth in SEQ ID NO:29, with the exception that the first arginine residue or the last histidine residue of SEQ ID NO:29 is deleted or replaced with a different amino acid residue.

In some cases, a polypeptide can include the sequences set forth in SEQ ID NOS:28 and 19. In some cases, a polypeptide provided herein can contain an amino acid sequence that aligns to (a) the sequence set forth in SEQ ID NO:28 with five or less (e.g., five or less, four or less, three or less, two or less, one, or zero) amino acid additions, deletions, substitutions, or combinations thereof, and (b) the sequence set forth in SEQ ID NO:19 with two or less (e.g., two or less, one, or zero) amino acid additions, deletions, substitutions, or combinations thereof. For example, a polypeptide provided herein can contain the sequence set forth in SEQ ID NO:30, with the exception that the first glycine residue or the last histidine residue of SEQ ID NO:30 is deleted or replaced with a different amino acid residue.

A polypeptide provided herein can have any length. For example, a polypeptide provided herein can be between 17 and 45 (e.g., between 18 and 40, between 22 and 44, between 25 and 45, between 26 and 44, between 27 and 43, between 28 and 42, between 29 and 41, between 30 and 40, between 31 and 39, between 23 and 35, between 25 and 30, or between 30 and 35) amino acid residues in length. It will be appreciated that a polypeptide with a length of 17 or 45 amino acid residues is a polypeptide with a length between 17 and 45 amino acid residues.

Variant NPs having conservative and/or non-conservative substitutions (e.g., with respect to any of SEQ ID NOS:1 to 30), as well as fragments of any of SEQ ID NOS:1 to 30, fragments of variants of any of SEQ ID NOS:1 to 30, and polypeptides comprising any of SEQ ID NOS:1 to 30, variants or fragments of any of SEQ ID NOS:1 to 30, or fragments of variants of any of SEQ ID NOS:1 to 30, can be screened for biological activity using any suitable assays, including those described herein. For example, the activity of a NP as described herein can be evaluated in vitro by testing its ability to suppress proliferation of HAoSMC. Cells can be exposed to a NP (e.g., $10^{-9}$ to $10^{-4}$ M ANP, BNP, CNP, CD-NP, CU-NP, ABC-NP, ABC-NP1, or BC-NP2), and samples can be assayed to evaluate the NP effects on cell proliferation. Cell proliferation can be detected and measured using, for example, a colormetric bromodeoxyuridine (BrdU) cell proliferation ELISA (Roche, Indianapolis, Ind.).

The activity of a NP also can be evaluated in vivo by, for example, testing its effects on factors such as pulmonary capillary wedge pressure, right atrial pressure, mean arterial pressure, urinary sodium excretion, urine flow, proximal and distal fractional sodium reabsorption, plasma renin activity, plasma cGMP levels, urinary cGMP excretion, net renal generation of cGMP, glomerular filtration rate, and left ventricular mass in animals. In some cases, such parameters can be evaluated after induced MI (e.g., MI induced by coronary artery ligation).

In some embodiments, the NPs provided herein can be cyclic due to disulfide bonds between cysteine residues (see, e.g., the ANP, BNP, CNP, and DNP structures depicted in FIG. 1). In some embodiments, a sulfhydryl group on a cysteine residue can be replaced with an alternative group (e.g., —$CH_2CH_2$—). To replace a sulfhydryl group with a —$CH_2$- group, for example, a cysteine residue can be replaced by alpha-aminobutyric acid. Such cyclic analog polypeptides can be generated, for example, in accordance with the methodology of Lebl and Hruby ((1984) *Tetrahedron Lett.* 25:2067), or by employing the procedure disclosed in U.S. Pat. No. 4,161,521.

In addition, ester or amide bridges can be formed by reacting the OH of serine or threonine with the carboxyl group of aspartic acid or glutamic acid to yield a bridge having the structure —$CH_2CO_2CH_2$—. Similarly, an amide can be obtained by reacting the side chain of lysine with aspartic acid or glutamic acid to yield a bridge having the structure —$CH_2C(O)NH(CH)_4$—. Methods for synthesis of these bridges are known in the art (see, e.g., Schiller et al. (1985) *Biochem. Biophy. Res. Comm.* 127:558, and Schiller et al. (1985) *Int. J. Peptide Protein Res.* 25:171). Other bridge-forming amino acid residues and reactions are provided in, for example, U.S. Pat. No. 4,935,492. Preparation of peptide analogs that include non-peptidyl bonds to link amino acid residues also are known in the art. See, e.g., Spatola et al. (1986) *Life Sci.* 38:1243; Spatola (1983) *Vega Data* 1(3); Morley (1980) *Trends Pharm. Sci.* 463-468; Hudson et al. (1979) *Int. J. Pept. Prot. Res.* 14:177; Spatola, in *Chemistry and Biochemistry of Amino Acid Peptides and Proteins*, B. Weinstein, ed., Marcel Dekker, New York, p. 267 (1983); Hann (1982) *J. Chem. Soc. Perkin Trans.* 1:307; Almquist et al. (1980) *J. Med. Chem.* 23:1392; Jennings-White et al. (1982) *Tetrahedron Lett.* 23:2533; European Patent Application EP 45665; Holladay et al. (1983) *Tetrahedron Lett.* 24:4401; and Hruby (1982) *Life Sci.* 31:189.

In some embodiments, a NP can comprise an amino acid sequence as set forth in SEQ ID NOS:1, 2, 3, 4, 5, 8, 9, 13, 16, 17, 18, 20, 22, 24, 25, 27, 29, or 30, but with a particular number of amino acid substitutions. For example, a NP can have the amino acid sequence of any one of SEQ ID NOS:1, 2, 3, 4, 5, 8, 9, 13, 16, 17, 18, 20, 22, 24, 25, 27, 29, or 30, but with one, two, three, four, or five amino acid substitutions. Examples of such amino acid sequences include, without limitation, those set forth in SEQ ID NOS:31-150.

In some embodiments, a NP as provided herein can include an amino acid sequence with at least 85% (e.g., 85%, 86%, 87%, 88%, 89%, 90%, 91%, 92%, 93%, 94%, 95%, 96%, 97%, 97.5%, 98%, 98.5%, 99.0%, 99.5%, 99.6%, 99.7%, 99.8%, 99.9%, or 100%) sequence identity to a region of a reference NP sequence (e.g., SEQ ID NOS:1-30). Percent sequence identity is calculated by determining the number of matched positions in aligned amino acid sequences, dividing the number of matched positions by the total number of aligned amino acids, and multiplying by 100. A matched position refers to a position in which identical amino acids occur at the same position in aligned amino acid sequences. Percent sequence identity also can be determined for any nucleic acid sequence.

Percent sequence identity is determined by comparing a target nucleic acid or amino acid sequence to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained on the World Wide Web from Fish & Richardson's web site (fr.com/blast) or the U.S. government's National Center for Biotechnology Information web site (ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a target sequence that is 30 amino acids in length is compared to the sequence set forth in SEQ ID NO:2, (2) the Bl2seq program presents 27 amino acids from the target sequence aligned with a region of the sequence set forth in SEQ ID NO:2 where the first and last amino acids of that 27 amino acid region are matches, and (3) the number of matches over those 27 aligned amino acids is 25, then the 30 amino acid target sequence contains a length of 27 and a percent identity over that length of 92.6 (i.e., 25÷27×100=92.6).

It will be appreciated that different regions within a single amino acid or nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated polypeptides can be produced using any suitable methods, including solid phase synthesis, and can be generated using manual techniques or automated techniques (e.g., using an Applied BioSystems (Foster City, Calif.) Peptide Synthesizer or a Biosearch Inc. (San Rafael, Calif.) automatic peptide synthesizer. Disulfide bonds between cysteine residues can be introduced by mild oxidation of the linear polypeptides using KCN as taught, e.g., in U.S. Pat. No. 4,757,048. NPs also can be produced recombinantly, as described herein.

In some cases, a polypeptide provided herein can be a substantially pure polypeptide. As used herein, the term "substantially pure" with reference to a polypeptide means that the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure or is any chemically synthesized polypeptide. A substantially pure polypeptide can be at least about 60, 65, 70, 75, 80, 85, 90, 95, or 99 percent pure. Typically, a substantially pure polypeptide will yield a single major band on a non-reducing polyacrylamide gel.

Salts of carboxyl groups of polypeptides can be prepared by contacting the peptide with one or more equivalents of a desired base such as, for example, a metallic hydroxide base (e.g., sodium hydroxide), a metal carbonate or bicarbonate base (e.g., sodium carbonate or sodium bicarbonate), or an amine base (e.g., triethylamine, triethanolamine, and the like). Acid addition salts of polypeptides can be prepared by contacting the polypeptide with one or more equivalents of an inorganic or organic acid (e.g., hydrochloric acid).

Esters of carboxyl groups of polypeptides can be prepared using any suitable means (e.g., those known in the art) for converting a carboxylic acid or precursor to an ester. For example, one method for preparing esters of the present polypeptides, when using the Merrifield synthesis technique, is to cleave the completed polypeptide from the resin in the presence of the desired alcohol under either basic or acidic conditions, depending upon the resin. The C-terminal end of the polypeptide then can be directly esterified when freed from the resin, without isolation of the free acid.

Amides of polypeptides can be prepared using techniques (e.g., those known in the art) for converting a carboxylic acid group or precursor to an amide. One method for amide formation at the C-terminal carboxyl group includes cleaving the polypeptide from a solid support with an appropriate amine, or cleaving in the presence of an alcohol, yielding an ester, followed by aminolysis with the desired amine.

N-acyl derivatives of an amino group of a polypeptide can be prepared by utilizing an N-acyl protected amino acid for the final condensation, or by acylating a protected or unprotected peptide. O-acyl derivatives can be prepared for example, by acylation of a free hydroxy peptide or peptide resin. Either acylation may be carried out using standard acylating reagent such as acyl halides, anhydrides, acyl imidazoles, and the like. Both N- and O-acylation may be carried out together, if desired.

In some embodiments, the NPs provided herein can have half-lives that are increased relative to the half-life of native NPs. For example, while the half-life of CNP after administration to a mammal is short (about a minute and a half), the elimination half-life of a chimeric NP such as CUB-NP or CAB-NP can be increased. ANP provided herein can have a half life that is increased by at least 2-fold (e.g., at least 2-fold, at least 3-fold, at least 4-fold, at least 5-fold, at least 6-fold, at least 7-fold, at least 8-fold, at least 9-fold, or at least 10-fold) as compared to a native NP such as CNP, for example. In some embodiments, a NP can have an elimination half-life of at least about 10 minutes (e.g., at least about 10 minutes, at least about 12 minutes, at least about 15 minutes, at least about 17 minutes, at least about 18 minutes, or at least about 20 minutes).

In some embodiments, a NP can be modified by linkage to a polymer such as polyethylene glycol (PEG), or by fusion to another polypeptide such as albumin, for example. For example, one or more PEG moieties can be conjugated to a NP via lysine residues. Linkage to PEG or another suitable polymer, or fusion to albumin or another suitable polypeptide can result in a modified NP having an increased half life as compared to an unmodified NP. Without being bound by a particular mechanism, an increased serum half life can result from reduced proteolytic degradation, immune recognition, or cell scavenging of the modified NP. Methods for modifying a polypeptide by linkage to PEG (also referred to as "PEGylation") or other polymers are known in the art, and include those set forth in U.S. Pat. No. 6,884,780; Cataliotti et al. ((2007) *Trends Cardiovasc. Med.* 17:10-14; Veronese and Mero (2008) *BioDrugs* 22:315-329; Miller et al. (2006) *Bioconjugate Chem.* 17:267-274; and Veronese and Pasut (2005) *Drug Discov. Today* 10:1451-1458, all of which are incorporated herein by reference in their entirety. Methods for modifying a polypeptide by fusion to albumin also are known in the art, and include those set forth in U.S. Patent Publication No. 20040086976, and Wang et al. (2004) *Pharm. Res.* 21:2105-2111, both of which are incorporated herein by reference in their entirety.

A NP as provided herein can function through the one or more of the guanylyl cyclase receptors through which the native NPs function. For example, in some embodiments, a NP as provided herein can bind to and function through the NPR-A receptor through which ANP and BNP function. In some cases, a NP can bind to and function through the NPR-A receptor, as do ANP and BNP. In some cases, a NP as provided herein can function through the NPR-B receptor through which CNP functions. In some cases, a NP as provided herein can bind to and function through the NPR-C receptor. Further, in some cases, a NP as provided herein can bind to and function through more than one guanylyl cyclase receptor, including NPR-A and NPR-B, for example. Methods for evaluating which receptor is involved in function of a particular NP are known in the art. For example, glomeruli, which contain both NPR-A and NPR-B, can be isolated (e.g., from a laboratory animal such as a dog) and incubated with a NP (e.g., a native, chimeric, or mutated NP), and cGMP levels can be measured. Glomeruli can be pretreated with antagonists of NPR-A or NPR-B to determine whether cGMP production stimulated by a NP through one or the other receptor can be attenuated.

In some cases, compounds (e.g., isolated NPs) provided herein can reduce or prevent restenosis. To determine whether a particular compound has the ability to reduce or prevent restenosis, one can carry out assays that are well known in the art, including those described herein (e.g., in the Example below).

Nucleic Acids, Vectors, and Host Cells

This document also describes exemplary nucleic acids encoding polypeptides (e.g., NPs), as well as expression vectors containing the nucleic acids, and host cells containing the nucleic acids and/or expression vectors. As used herein, the term "nucleic acid" refers to both RNA and DNA, including cDNA, genomic DNA, and synthetic (e.g., chemically synthesized) DNA. A nucleic acid molecule can be double-stranded or single-stranded (i.e., a sense or an antisense single strand). Nucleic acids include, for example, cDNAs encoding the NPs, variant NPs, and chimeric NPs provided herein.

An "isolated nucleic acid" is a nucleic acid that is separated from other nucleic acid molecules that are present in a vertebrate genome, including nucleic acids that normally flank one or both sides of the nucleic acid in a vertebrate genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid. By way of example and not limitation, an "isolated ANP nucleic acid," for example, can be a RNA or DNA molecule containing 9 or more (e.g., 15 or more, 21 or more, 36 or more, or 45 or more) sequential nucleotide bases that encode at least a portion of ANP, or a RNA or DNA complementary thereto.

Also provided herein are nucleic acid molecules that can selectively hybridize under stringent hybridization conditions to a nucleic acid molecule encoding a NP (e.g., nucleic acid molecules encoding polypeptides having the amino acid sequences set forth in SEQ ID NOS:1, 2, 3, 4, 5, 8, 9, 13, 16, 17, 18, 20, 22, 24, 25, 27, 29, and 30, or variants and fragments thereof. The term "selectively hybridize" means to detectably and specifically bind under hybridization and wash conditions that minimize appreciable amounts of detectable binding to nonspecific nucleic acids. For example, high stringency conditions can be used to achieve selective hybridization conditions. Moderate and stringent hybridization conditions include those that are well known in the art. See, for example, sections 9.47-9.51 of Sambrook et al. (1989). As used herein, stringent conditions are those that (1) employ low ionic strength and high temperature for washing, such as 0.015 M NaCl/0.0015 M sodium citrate (SSC) with 0.1% sodium lauryl sulfate (SDS) at 50° C., or (2) employ a denaturing agent such as formamide during hybridization, such as 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Alternatively, 50% formamide, 5×SSC (0.75 M NaCl, 0.075 M sodium citrate), 50 mM sodium phosphate (pH 6.8), 0.1% sodium phosphate, 5×Denhardt's solution, sonicated salmon sperm DNA (50 µg/ml), 0.1% sodium dodecylsulfate (SDS), and 10% dextran sulfate at 42° C. can be used, with washes at 42° C. in 0.2×SSC and 0.1% SDS.

Isolated nucleic acid molecules can be produced using standard techniques, including, without limitation, common molecular cloning and chemical nucleic acid synthesis techniques. For example, polymerase chain reaction (PCR) techniques can be used to obtain an isolated nucleic acid containing nucleotide sequence that encodes a NP as provided herein. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids (e.g., nucleic acids encoding variant NPs) also can be obtained by mutagenesis. For example, a reference sequence can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992. Non-limiting examples of variant NPs art provided herein.

This document also contemplates nucleic acid molecules encoding amino acid sequences from NPs other than ANP, BNP, CNP, DNP, URO, or chimeras or variants thereof. Sources of nucleotide sequences from which nucleic acid molecules encoding a NP, or the nucleic acid complement thereof, can be obtained include total or polyA+ RNA from any eukaryotic source, including reptilian (e.g., snake) or mammalian (e.g., human, rat, mouse, canine, bovine, equine, ovine, caprine, or feline) cellular source from which cDNAs can be derived by methods known in the art. Other sources of the nucleic acid molecules provided herein include genomic libraries derived from any eukaryotic cellular source, including mammalian sources as exemplified above.

Nucleic acid molecules encoding native NPs can be identified and isolated using standard methods, e.g., as described by Sambrook et al., *Molecular Cloning: A Laboratory Manual*, Cold Spring Harbor Laboratory Press, NY (1989). For example, reverse-transcriptase PCR(RT-PCR) can be used to isolate and clone NP cDNAs from isolated RNA that contains RNA sequences of interest (e.g., total RNA isolated from human tissue). Other approaches to identify, isolate and clone NP cDNAs include, for example, screening cDNA libraries.

Vectors containing nucleic acids such as those described herein also are provided. A "vector" is a replicon, such as a plasmid, phage, or cosmid, into which another DNA segment may be inserted so as to bring about the replication of the inserted segment. An "expression vector" is a vector that includes one or more expression control sequences, and an "expression control sequence" is a DNA sequence that controls and regulates the transcription and/or translation of another DNA sequence.

In the expression vectors provided herein, a nucleic acid (e.g., a nucleic acid encoding a NP) can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 to 500 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence. Expression vectors thus can be useful to produce antibodies as well as other multivalent molecules.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

Host cells containing vectors also are provided. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Suitable methods for transforming and transfecting host cells can be found, for example, in Sambrook et al., *Molecular Cloning: A Laboratory Manual* ($2^{nd}$ edition), Cold Spring Harbor Laboratory, New York (1989). For example, calcium phosphate precipitation, electroporation, heat shock, lipofection, microinjection, and viral-mediated nucleic acid transfer can be used introduce nucleic acid into cells. In addition, naked DNA can be delivered directly to cells in vivo as described elsewhere (U.S. Pat. Nos. 5,580,859 and 5,589,466).

Detecting Polypeptides

This document provides methods and materials for detecting a polypeptide provided herein. Such methods and materials can be used to monitor polypeptide levels within a mammal receiving the polypeptide as a therapeutic. A NP provided herein can be detected, for example, immunologically, using one or more antibodies. As used herein, the term "antibody" includes intact molecules as well as fragments thereof that are capable of binding to an epitopic determinant of a polypeptide provided herein. The term "epitope" refers to an antigenic determinant on an antigen to which the paratope of an antibody binds. Epitopic determinants usually consist of chemically active surface groupings of molecules such as amino acids or sugar side chains, and typically have specific three-dimensional structural characteristics, as well as specific charge characteristics. Epitopes generally have at least five contiguous amino acids (a continuous epitope), or alternatively can be a set of noncontiguous amino acids that define a particular structure (e.g., a conformational epitope). The term "antibody" includes polyclonal antibodies, monoclonal antibodies, humanized or chimeric antibodies, single chain Fv antibody fragments, Fab fragments, and $F(ab)_2$ fragments. Polyclonal antibodies are heterogeneous populations of antibody molecules that are contained in the sera of the immunized animals. Monoclonal antibodies are homogeneous populations of antibodies to a particular epitope of an antigen.

Antibody fragments that have specific binding affinity for a NP provided herein can be generated by known techniques. For example, F(ab')2 fragments can be produced by pepsin digestion of the antibody molecule; Fab fragments can be generated by reducing the disulfide bridges of F(ab')2 fragments. In some cases, Fab expression libraries can be constructed. See, for example, Huse et al., *Science*, 246:1275 (1989). Once produced, antibodies or fragments thereof can be tested for recognition of a polypeptide provided herein by standard immunoassay methods including ELISA techniques, radioimmunoassays, and Western blotting. See, *Short Protocols in Molecular Biology*, Chapter 11, Green Publishing Associates and John Wiley & Sons, Ed. Ausubel et al., 1992.

In immunological assays, an antibody having specific binding affinity for a polypeptide provided herein or a secondary antibody that binds to such an antibody can be labeled, either directly or indirectly. Suitable labels include, without limitation, radionuclides (e.g., $^{125}I$, $^{131}I$, $^{35}S$, $^{3}H$, $^{32}P$, $^{33}P$, or $^{14}C$), fluorescent moieties (e.g., fluorescein, FITC, PerCP, rhodamine, or PE), luminescent moieties (e.g., Qdot™ nanoparticles supplied by Invitrogen (Carlsbad, Calif.)), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Immunological assays for detecting a polypeptide provided herein can be performed in a variety of known formats, including sandwich assays, competition assays (competitive RIA), or bridge immunoassays. See, for example, U.S. Pat. Nos. 5,296,347; 4,233,402; 4,098,876; and 4,034,074. Methods of detecting a polypeptide provided herein generally include contacting a biological sample with an antibody that binds to a polypeptide provided herein and detecting binding of the polypeptide to the antibody. For example, an antibody having specific binding affinity for a polypeptide provided herein can be immobilized on a solid substrate by any of a variety of methods known in the art and then exposed to the biological sample. Binding of the polypeptide to the antibody on the solid substrate can be detected by exploiting the phenomenon of surface plasmon resonance, which results in a change in the intensity of surface plasmon resonance upon binding that can be detected qualitatively or quantitatively by an appropriate instrument, e.g., a Biacore apparatus (Biacore International AB, Rapsgatan, Sweden). In some cases, the antibody can be labeled and detected as described above. A standard curve using known quantities of a polypeptide provided herein can be generated to aid in the quantitation of the levels of the polypeptide.

In some embodiments, a "sandwich" assay in which a capture antibody is immobilized on a solid substrate can be used to detect the presence, absence, or level of a polypeptide provided herein. The solid substrate can be contacted with the biological sample such that any polypeptide of interest in the sample can bind to the immobilized antibody. The presence, absence, or level of the polypeptide bound to the antibody can be determined using a "detection" antibody having specific binding affinity for the polypeptide. In some embodiments, a capture antibody can be used that has binding affinity for ANP, BNP, CNP, DNP, and/or URO, or a chimeric or variant polypeptide as described herein, and a detection antibody can be used that has specific binding affinity for a particular polypeptide provided herein (e.g., a polypeptide having the amino acid sequence set forth in any of SEQ ID NOS:1, 2, 3, 4, 5, 8, 9, 13, 16, 17, 18, 20, 22, 24, 25, 27, or 30). It is understood that in sandwich assays, the capture antibody should not bind to the same epitope (or range of epitopes in the case of a polyclonal antibody) as the detection antibody. Thus, if a monoclonal antibody is used as a capture antibody, the detection antibody can be another monoclonal antibody that binds to an epitope that is either physically separated from or only partially overlaps with the epitope to which the capture monoclonal antibody binds, or a polyclonal antibody that binds to epitopes other than or in addition to that to which the capture monoclonal antibody binds. If a polyclonal antibody is used as a capture antibody, the detection antibody can be either a monoclonal antibody that binds to an epitope that is either physically separated from or partially overlaps with any of the epitopes to which the capture polyclonal antibody binds, or a polyclonal antibody that binds to epitopes other than or in addition to that to which the capture polyclonal antibody binds. Sandwich assays can be performed as sandwich ELISA assays, sandwich Western blotting assays, or sandwich immunomagnetic detection assays.

Suitable solid substrates to which an antibody (e.g., a capture antibody) can be bound include, without limitation, microtiter plates, tubes, membranes such as nylon or nitrocellulose membranes, and beads or particles (e.g., agarose, cellulose, glass, polystyrene, polyacrylamide, magnetic, or magnetizable beads or particles). Magnetic or magnetizable particles can be particularly useful when an automated immunoassay system is used.

Antibodies having specific binding affinity for a polypeptide provided herein can be produced through standard methods. For example, a polypeptide can be recombinantly produced as described above, can be purified from a biological sample (e.g., a heterologous expression system), or can be chemically synthesized, and used to immunize host animals, including rabbits, chickens, mice, guinea pigs, or rats. For example, a polypeptide having the amino acid sequence set forth in any of SEQ ID NOS:1, 2, 3, 4, 5, 8, 9, 13, 16, 17, 18, 20, 22, 24, 25, 27, 29, 30, or fragments or variants thereof that are at least six amino acids in length, can be used to immunize an animal. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Monoclonal antibodies can be prepared using a polypeptide provided herein and standard hybridoma technology. In particular, monoclonal antibodies can be obtained by any technique that provides for the production of antibody molecules by continuous cell lines in culture such as described by Kohler et al., *Nature*, 256:495 (1975), the human B-cell hybridoma technique (Kosbor et al., *Immunology Today*, 4:72 (1983); Cote et al., *Proc. Natl. Acad. Sci. USA*, 80:2026 (1983)), and the EBV-hybridoma technique (Cole et al., "Monoclonal Antibodies and Cancer Therapy," Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies can be cultivated in vitro and in vivo.

Other techniques for detecting a polypeptide provided herein include mass-spectrophotometric techniques such as electrospray ionization (ESI), and matrix-assisted laser desorption-ionization (MALDI). See, for example, Gevaert et al., *Electrophoresis*, 22:1645-51 (2001); Chaurand et al., *J. Am. Soc. Mass Spectrom.*, 10:91-103 (1999). Mass spectrometers useful for such applications are available from Applied Biosystems (Foster City, Calif.); Bruker Daltronics (Billerica, Mass.); and Amersham Pharmacia (Sunnyvale, Calif.).

Compositions and Methods for Administration

The compounds described herein (e.g., native NPs, as well as chimeric and variant NPs), or nucleic acids encoding the polypeptides described herein, can be incorporated into compositions for administration to a subject (e.g., a subject suffering from or at risk for restenosis). Thus, this document provides, for example, the use of compounds as described herein in the manufacture of medicaments for treating (e.g., reducing) restenosis. Methods for formulating and subsequently administering therapeutic compositions are well known to those in the art. Dosages typically are dependent on the responsiveness of the subject to the compound, with the course of treatment lasting from several days to several months, or until a suitable response is achieved. Persons of ordinary skill in the art routinely determine optimum dosages, dosing methodologies and repetition rates. Optimum dosages can vary depending on the relative potency of an antibody, and generally can be estimated based on the $EC_{50}$ found to be effective in in vitro and/or in vivo animal models. Compositions containing the compounds (e.g., NPs) and nucleic acids provided herein may be given once or more daily, weekly, monthly, or even less often, or can be administered continuously for a period of time (e.g., hours, days, or weeks). For example, a NP or a composition containing a NP can be administered to a MI patient at a dose of at least about 0.01 ng NP/kg to about 100 mg NP/kg of body mass at or about the time of reperfusion, or can be administered continuously as an infusion beginning at or about the time of reperfusion and continuing for one to seven days (e.g., at a dose of about 0.01 ng NP/kg/minute to about 0.5 µg NP/kg/minute).

The NPs and nucleic acids can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption.

In some embodiments, a composition can contain a NP as provided herein in combination with a pharmaceutically acceptable carrier. Pharmaceutically acceptable carriers include, for example, pharmaceutically acceptable solvents, suspending agents, or any other pharmacologically inert vehicles for delivering antibodies to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water; saline solution; binding agents (e.g., polyvinylpyrrolidone or hydroxypropyl methylcellulose); fillers (e.g., lactose or dextrose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions containing molecules described herein can be administered by a number of methods, depending upon whether local or systemic treatment is desired. Administration can be, for example, parenteral (e.g., by subcutaneous, intrathecal, intraventricular, intramuscular, or intraperitoneal injection, or by intravenous (i.v.) drip); oral; topical (e.g., transdermal, sublingual, ophthalmic, or intranasal); or pulmonary (e.g., by inhalation or insufflation of powders or aerosols), or can occur by a combination of such methods. Administration can be rapid (e.g., by injection) or can occur over a period of time (e.g., by slow infusion or administration of slow release formulations).

Compositions and formulations for parenteral, intrathecal or intraventricular administration include sterile aqueous solutions (e.g., sterile physiological saline), which also can contain buffers, diluents and other suitable additives (e.g., penetration enhancers, carrier compounds and other pharmaceutically acceptable carriers).

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Formulations for topical administration include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be useful. In some embodiments, transdermal delivery of NPs as provided herein can be particularly useful. Methods and compositions for transdermal delivery include those described in the art (e.g., in Wermeling et al. (2008) *Proc. Natl. Acad. Sci. USA* 105:2058-2063; Goebel and Neubert (2008) *Skin Pharmacol. Physiol.* 21:3-9; Banga (2007) *Pharm. Res.* 24:1357-1359; Malik et al. (2007) *Curr Drug Deliv.* 4:141-151; and Prausnitz (2006) *Nat. Biotechnol.* 24:416-417).

Nasal preparations can be presented in a liquid form or as a dry product. Nebulized aqueous suspensions or solutions can include carriers or excipients to adjust pH and/or tonicity.

Pharmaceutical compositions include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsion formulations are particularly useful for oral delivery of therapeutic compositions due to their ease of formulation and efficacy of solubilization, absorption, and bioavailability. Liposomes can be particularly useful due to their specificity and the duration of action they offer from the standpoint of drug delivery.

Compositions provided herein can contain any pharmaceutically acceptable salts, esters, or salts of such esters, or any other compound which, upon administration to a subject, is capable of providing (directly or indirectly) the biologically active metabolite or residue thereof for the relevant compound (e.g., NP). Accordingly, for example, this document describes pharmaceutically acceptable salts of NPs, prodrugs and pharmaceutically acceptable salts of such prodrugs, and other bioequivalents. A prodrug is a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the NPs useful in methods provided herein (i.e., salts that retain the desired biological activity of the parent NPs without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); salts formed with organic acids (e.g., acetic acid, citric acid, oxalic acid, palmitic acid, or fumaric acid); and salts formed with elemental anions (e.g., bromine, iodine, or chlorine).

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions, such as dyes, flavoring agents, preservatives, antioxidants, opacifiers, thickening agents, and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, penetration enhancers, and aromatic substances. When added, however, such materials should not unduly interfere with the biological activities of the other components within the compositions.

In some cases, a polypeptide provided herein can be formulated as a sustained release dosage form. For example, a NP can be formulated into a controlled release formulation. In some cases, coatings, envelopes, or protective matrices can be formulated to contain one or more of the polypeptides provided herein. Such coatings, envelopes, and protective matrices can be used to coat indwelling devices such as stents, catheters, and peritoneal dialysis tubing. In some cases, a polypeptide provided herein can incorporated into a polymeric substances, liposomes, microemulsions, microparticles, nanoparticles, or waxes.

Pharmaceutical formulations as disclosed herein, which can be presented conveniently in unit dosage form, can be prepared according to conventional techniques well known in the pharmaceutical industry. Such techniques include the step of bringing into association the active ingredients (i.e., the antibodies) with the desired pharmaceutical carrier(s). Typically, the formulations can be prepared by uniformly and intimately bringing the active ingredients into association with liquid carriers or finely divided solid carriers or both, and then, if necessary, shaping the product. Formulations can be sterilized if desired, provided that the method of sterilization does not interfere with the effectiveness of the molecules(s) contained in the formulation.

Methods for Reducing or Preventing Restenosis

This document also provides methods for using compounds (e.g., NPs) as disclosed herein for reducing or preventing restenosis. Thus, the compounds and nucleic acid molecules provided herein can be administered to a mammal (e.g., a human or a non-human mammal) in order to reduce or prevent restenosis that can occur, for example, after angioplasty, stent placement, vascular surgery, cardiac surgery, or interventional radiology. The composition or NP can be administered at any suitable dose, depending on various factors including, without limitation, the agent chosen and the patient characteristics. Administration can be local or systemic.

In some embodiments, a NP or a composition containing a NP can be administered at a dose of at least about 0.01 ng NP/kg to about 100 mg NP/kg of body mass (e.g., about 10 ng NP/kg to about 50 mg NP/kg, about 20 ng NP/kg to about 10 mg NP/kg, about 0.1 ng NP/kg to about 20 ng NP/kg, about 3 ng NP/kg to about 10 ng NP/kg, or about 50 ng NP/kg to about 100 µg/kg) of body mass, although other dosages also may provide beneficial results. In some cases, a composition containing a NP can be administered as a continuous intravenous infusion beginning at or about the time of reperfusion (i.e., at the time an occluded artery is opened), and continuing for one to seven days (e.g., one, two, three, four, five, six, or seven days). Such a composition can be administered at a dose of, for example, about 0.1 ng NP/kg/minute to about 500 ng NP/kg/minute (e.g., about 0.5 ng NP/kg/minute, about 1 ng NP/kg/minute, about 2 ng NP/kg/minute, about 3 ng NP/kg/minute, about 5 ng NP/kg/minute, about 7.5 ng NP/kg/minute, about 10 ng NP/kg/minute, about 12.5 ng NP/kg/minute, about 15 ng NP/kg/minute, about 20 ng NP/kg/minute, about 25 ng NP/kg/minute, about 30 ng NP/kg/minute, about 50 ng NP/kg/minute, about 100 ng NP/kg/minute, or about 300 ng NP/kg/minute). In some embodiments, a composition containing a NP can be administered before reperfusion (e.g., about one hour prior to reperfusion), either as one or more individual doses or as a continuous infusion beginning about one hour prior to reperfusion). For example, a composition can be administered beginning about one hour, about 45 minutes, about 30 minutes, or about 15 minutes prior to reperfusion. In some cases, a composition containing a NP as provided herein can be administered after reperfusion (e.g., within about ten hours of reperfusion), and can be administered either as one or more individual doses or as a continuous infusion beginning within about ten hours of reperfusion. For example, a composition can be administered about one hour, about two hours, about three hours, about four hours, about five hours, about six hours, about seven hours, about eight hours, about nine hours, or about ten hours after reperfusion.

In some embodiments, a NP or a composition containing a NP can be administered via a first route (e.g., intravenously) for a first period of time, and then can be administered via another route (e.g., topically or subcutaneously) for a second period of time. For example, a composition containing a NP can be intravenously administered to a mammal (e.g., a human) at a dose of about 0.1 ng NP/kg/minute to about 300 ng NP/kg/minute (e.g., about 1 ng NP/kg/minute to about 15 ng NP/kg/minute, about 3 ng NP/kg/minute to about 10 ng NP/kg/minute, or about 10 ng NP/kg/minute to about 30 ng NP/kg/minute) for one to seven days (e.g., one, two, three, four, five, six, or seven days), and subsequently can be subcutaneously administered to the mammal at a dose of about 10 ng NP/kg/day to about 100 ng NP/kg/day (e.g., about 10 ng NP/kg/day, about 20 ng NP/kg/day, about 25 ng NP/kg/day, about 30 ng NP/kg/day, about 50 ng NP/kg/day, or about 100 ng NP/kg/day) for five to 30 days (e.g., seven, 10, 14, 18, 21, 24, or 27 days).

The methods provided herein can include administering to a mammal an effective amount of a NP (e.g., a native, chimeric, or variant NP) or a nucleic acid encoding a NP, or an effective amount of a composition containing such a molecule. As used herein, the term "effective amount" is an amount of a molecule or composition that is sufficient to reduce the occurrence of restenosis in a mammalian recipient by at least 10% (e.g., 10%, 15%, 20%, 25%, 30%, 40%, 50%, 60%, 70%, 75%, 80%, 85%, 90%, 95%, 99%, or 100%). The presence or extent of restenosis can be evaluated using methods known in the art, including, for example, angiogram.

In some embodiments, for example, an "effective amount" of a NP as provided herein can be an amount that reduces restenosis in a treated mammal by at least 10% as compared to the level of restenosis in the mammal prior to administration of the NP or without administration of the NP (e.g., the level of restenosis after a previous angioplasty or stent placement procedure for example), or as compared to the level of restenosis in a control, untreated mammal. The level of restenosis can be assessed using, for example, the methods described herein.

The invention will be further described in the following example, which does not limit the scope of the invention described in the claims.

Example

NPs Prevent Restenosis of Vasculature and Muscular Conduits

The effects of natural and chimeric natriuretic peptides on proliferation of HAoSMC were assessed. HAoSMC were incubated with increasing concentrations of natural natriuretic peptides (ANP, BNP, or CNP) or chimeric natriuretic peptides (CD-NP, CU-NP, ABC-NP, ABC-NP1, or BC-NP2). Cell proliferation studies were performed. Briefly, HAoSMC (passages 4 through 6; Clonetics Corporation Inc., San Diego, Calif.) were grown to confluence in culture media supplemented with required growth factors, and were passaged in 96 well plates and incubated with supplemented smooth muscle cell media for 24 hours. The supplemented medium was replaced with basal smooth muscle cell media for 24 hours to render the cells quiescent. The cells were subsequently incubated in the presence or absence of serum-supplemented media (5%), and in the presence of serum-supplemented growth media along with exogenous NPs ($10^{-9}$ to $10^{-4}$ M ANP, BNP, CNP, CD-NP, CU-NP, ABC-NP, ABC-NP1, or BC-NP2) for 24 hours. Proliferation was assessed by measuring bromodeoxyuridine (BrdU) uptake over the next 24 hours, as previously described (Schirger et al. (2000) *J. Am. Coll. Cardiol.* 35:796-801.)

Figure 2:
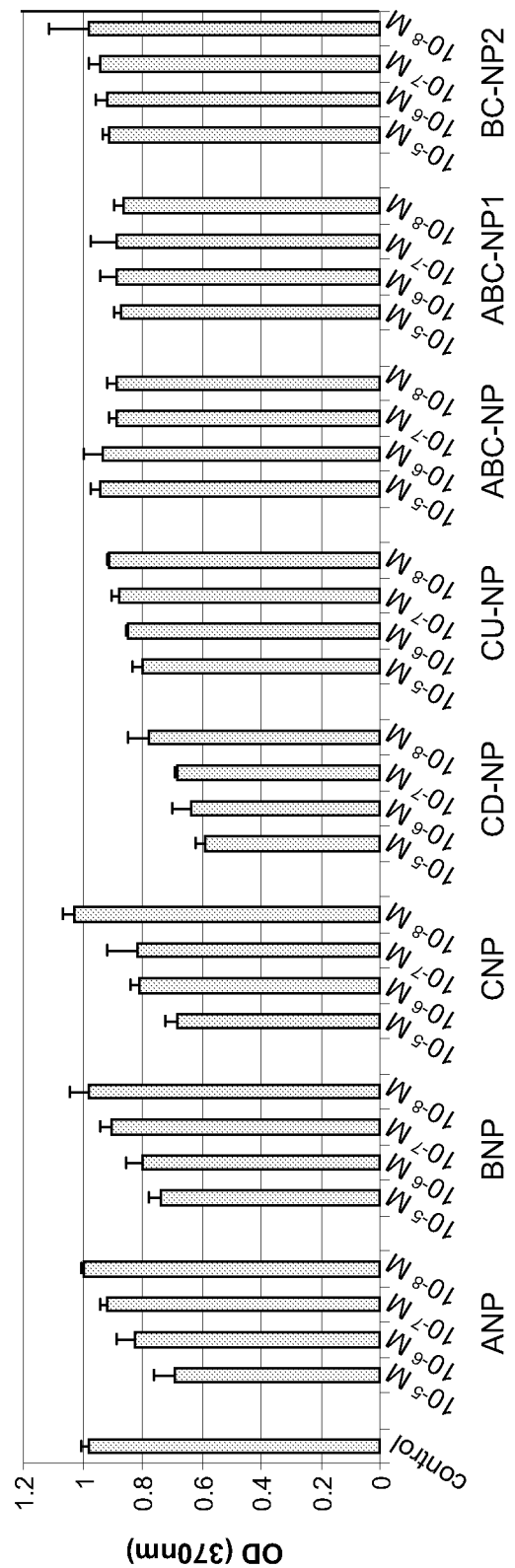
FIG. 2 is a graph plotting the effect of natriuretic polypeptides on HAoSMC proliferation.

Each of the NPs evaluated was found to have antiproliferative actions on HAoSMC (FIG. 2). Increasing concentrations of ANP reduced proliferation by about 10 percent ($10^{-7}$ M ANP), about 18 percent ($10^{-6}$ M ANP), and about 30 percent ($10^{-5}$ M ANP). Increasing concentrations of BNP reduced proliferation by about 10 percent ($10^{-7}$ M BNP), about 20 percent ($10^{-6}$ M BNP), and about 25 percent ($10^{-5}$ M BNP). Increasing concentrations of CNP reduced proliferation by about 20 percent ($10^{-7}$ M and $10^{-6}$ M CNP) and about 30 percent ($10^{-5}$ M CNP). Increasing concentrations of CD-NP had the greatest effect, decreasing proliferation by about 22 percent ($10^{-8}$ M CD-NP), about 30 percent ($10^{-7}$ M CD-NP), about 35 percent ($10^{-6}$ M CD-NP), and about 40 percent ($10^{-5}$ M CD-NP). Increasing concentrations of CU-NP reduced proliferation by about 8 percent ($10^{-8}$ M CU-NP), about 10 percent ($10^{-7}$ M CU-NP), about 15 percent ($10^{-6}$ M CU-NP), and about 20 percent ($10^{-5}$ M CU-NP). ABC-NP, ABC-NP1, and BC-NP2 reduced proliferation by about 5 percent ($10^{-5}$ M and $10^{-6}$ M ABC-NP, and $10^{-7}$ M BP-NP2), about 10 percent ($10^{-7}$ M and $10^{-8}$ M ABC-NP, $10^{-6}$ M and $10^{-7}$ M ABC-NP1, and $10^{-5}$ M and $10^{-6}$ M BC-NP2), or about 15 percent ($10^{-5}$ M and $10^{-8}$ M ABC-NP1). Thus, natural and chimeric NPs may be useful to prevent restenosis of the vasculature and muscular conduits.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing restenosis in a subject identified as being in need thereof, comprising administering to said subject a therapeutically effective amount of a composition comprising a pharmaceutically acceptable carrier and a natriuretic polypeptide under conditions wherein restenosis in said subject is reduced, wherein said natriuretic polypeptide comprises the amino acid sequence set forth in SEQ ID NO: 9, or the amino acid sequence set forth in SEQ ID NO: 9 with one, two, three, four, or five amino acid substitutions relative to the sequence set forth in SEQ ID NO: 9.

2. A method for reducing restenosis in a subject identified as being in need thereof, comprising administering to said subject a therapeutically effective amount of a composition comprising a pharmaceutically acceptable carrier and a natriuretic polypeptide under conditions wherein restenosis in said subject is reduced, wherein said natriuretic polypeptide comprises the amino acid sequence set forth in SEQ ID NO:13, or the amino acid sequence set forth in SEQ ID NO:13 with one, two, three, four, or five amino acid substitutions relative to the sequence set forth in SEQ ID NO:13.

* * * * *